United States Patent
Datt et al.

(10) Patent No.: US 11,957,815 B2
(45) Date of Patent: Apr. 16, 2024

(54) READY TO USE BIODEGRADABLE AND BIOCOMPATIBLE CELL-BASED NERVE CONDUIT FOR NERVE INJURY AND A METHOD OF PREPARATION THEREOF

(71) Applicant: DATT LIFE SCIENCES PRIVATE LIMITED, New Delhi (IN)

(72) Inventors: Rajan Datt, New Delhi (IN); Siddharth Pandey, New Delhi (IN); Poonam Meena, New Delhi (IN); Mukesh Kumar, New Delhi (IN); Nitin Khatri, New Delhi (IN); Rakesh Kumar Nagar, New Delhi (IN)

(73) Assignee: DATT LIFE SCIENCES PRIVATE LIMITED, New Delhi (IN)

( * ) Notice: Subject to any disclaimer, the term of this patent is extended or adjusted under 35 U.S.C. 154(b) by 700 days.

(21) Appl. No.: 17/095,997

(22) Filed: Nov. 12, 2020

(65) Prior Publication Data

US 2022/0016320 A1    Jan. 20, 2022

(30) Foreign Application Priority Data

Jul. 17, 2020    (IN) .............................. 202011030484

(51) Int. Cl.

| | |
|---|---|
| A61K 9/20 | (2006.01) |
| A61L 27/26 | (2006.01) |
| A61L 27/54 | (2006.01) |
| A61L 27/58 | (2006.01) |
| C12N 5/0775 | (2010.01) |

(52) U.S. Cl.
CPC .............. *A61L 27/58* (2013.01); *A61L 27/26* (2013.01); *A61L 27/54* (2013.01); *C12N 5/0668* (2013.01); *C12N 2513/00* (2013.01); *C12N 2533/40* (2013.01); *C12N 2533/54* (2013.01); *C12N 2533/72* (2013.01); *C12N 2537/10* (2013.01)

(58) Field of Classification Search
CPC .......... A61L 27/58; A61L 27/26; A61L 27/54; A61L 2430/32; A61L 27/383; A61L 27/56; C12N 5/0668; C12N 2513/00; C12N 2533/40; C12N 2533/54; C12N 2533/72; C12N 2537/10
See application file for complete search history.

(56) References Cited

U.S. PATENT DOCUMENTS

| | | |
|---|---|---|
| 3,786,817 A | 1/1974 | Palma |
| 4,534,349 A | 8/1985 | Barrows |
| 5,019,087 A | 5/1991 | Nichols |
| 10,507,187 B2 | 12/2019 | Jackson et al. |
| 2012/0165957 A1 | 6/2012 | Everland et al. |
| 2015/0118197 A1 | 4/2015 | Claeyssens et al. |

FOREIGN PATENT DOCUMENTS

| | | | | |
|---|---|---|---|---|
| CN | 1589913 | | 3/2005 | |
| CN | 108310467 A | * | 7/2018 | ............. A61L 27/20 |
| EP | 3326660 A1 | * | 5/2018 | ............. A61L 27/26 |
| GB | 2386841 | | 1/2003 | |
| WO | 2004/087231 | | 10/2004 | |

OTHER PUBLICATIONS

Wang et al. Materials Science and Engineering C 71 (2017) 308-316. (Year: 2017).*
Alam et al. ACS Sustainable Chem. Eng. 2018, 6, 8736-8742. (Year: 2018).*
Nitta Gelatin. Gelatin Handbook. Obtained from <https://nitta-gelatin.com/wp-content/uploads/2018/02/GMIA_Gelatin-Handbook.pdf>. (Year: 2018).*
Indian Patent Application No. 201821042296 Filing Date: Nov. 9, 2018 Inventor(s): D.Y. Patil Vidyapeeth.

* cited by examiner

*Primary Examiner* — Mina Haghighatian
*Assistant Examiner* — Janice Y Silverman
(74) *Attorney, Agent, or Firm* — ALLEN, DYER, DOPPELT + GILCHRIST, P.A.

(57) ABSTRACT

An artificial tissue construct for nerve repair and regeneration includes a biocompatible and biodegradable nerve guidance matrix comprising a plurality of biopolymers that include chitosan, gelatin, collagen and hyaluronic acid. A cross-linker includes glutaraldehyde. The nerve guidance matrix is formed as a three-dimensional scaffold polyelectrolyte complex (PEC). A subconfluent and grown monolayer of at least one of human mesenchymal stem cells, mesenchymal stem cells, differentiated Schwann cells and neuronal cells is on the biocompatible and biodegradable nerve guidance matrix for direct implantation or delivery. A method of making the artificial tissue construct is disclosed.

8 Claims, 16 Drawing Sheets

READY TO USE BIODEGRADABLE AND BIOCOMPATIBLE CELL-BASED NERVE CONDUIT FOR NERVE INJURY AND A METHOD OF PREPARATION THEREOF

FIELD OF THE INVENTION

The present invention relates to the field of nerve tissue engineering.

More particularly, the invention relates a novel in-vitro method for inducing cells to produce a tissue engineered construct for nerve regeneration and repair in a synergistic manner.

More particularly, the invention relates to a living cells-based nerve conduit/matrix, which has tissue like properties and is capable of being used for nerve regeneration and repair.

More particularly, the invention relates to a cells-based nerve conduit/matrix for the treatment of peripheral nerve injury (PNI), spinal cord injury and any other type of nerve injuries.

BACKGROUND AND PRIOR ART OF THE INVENTION

The field of tissue engineering combines bioengineering methods with the principles of life sciences to understand the structural and functional relationships in normal and pathological mammalian tissues. The goal of tissue engineering is the development and ultimate application of biological substitutes to restore, maintain, or improve tissue functions. Thus, through tissue engineering, it is possible to design and manufacture a bioengineered tissue construct in vitro. Bioengineered tissues construct include cells that are associated with a human tissues and natural matrix/scaffold. The new bioengineered tissue must be functional when grafted onto a host, and be permanently incorporated within the host's body or progressively bio-remodeled by cells from the recipient host patient. Fabrication of a tissue equivalent without a support member or scaffold leads to scientific challenges in creating the new bioengineered tissue.

The peripheral nervous system (PNS) extends outside the central nervous system (CNS) and provides the functions of, amongst other things, bringing sensory information to the CNS and receiving motor commands from the CNS, coordinating body movements and controlling the involuntary muscles. Unlike the central nervous system, the PNS is not protected by bone and is therefore vulnerable to injuries.

Damage to nerves of the PNS can cause significant motor or sensory impairment. In particular, patients with acute peripheral nerve injury usually have nerve conduction defects that can manifest as motor impairment or sensory dysfunction. Depending on the severity of the injury and the nerve affected, a severed nerve may cause paralysis, partial loss of mobility of the affected limb and/or a loss of sensation. Nerve and muscle atrophy will follow if no sufficient recovery occurs or no timely treatment is provided. Similarly, crush damage to peripheral nerves can result in reduced motor or sensory performance.

Injuries to peripheral nerves can be caused by trauma, Surgery, cancer and by congenital anomalies. Injuries to peripheral nerves can be also caused by radiation therapy, chemotherapy, metabolic/endocrine complications, inflammatory and autoimmune diseases, vitamin deficiencies, infectious diseases, toxic causes, accidental exposure to organic metals and heavy metals, drugs, amputations and disease or condition relating to a loss of motor or sensory nerve function. Nerve injury or lesion may include nerve transection, crush, compression, stretch, laceration (sharps or bone fragments), ischemia and blast. In addition, nerve injury or lesion may result from damage or disruption of the neuronal axons.

Peripheral nerve injury is a major source of morbidity and an area with significant medical need. Indeed, only 50% of patients achieve good to normal restoration of function following Surgical repair, regardless of the strategy. Moreover, failure of nerve regeneration may necessitate amputation of an otherwise salvaged limb. This stems from the inadequacy of current PNI repair strategies, where even the "gold-standard treatment—the nerve autograft is largely ineffective for major nerve trauma, defined as loss of a large segment of nerve (i.e. >5 cm) or injury occurring closer to the spinal cord (e.g., shoulder, thigh) resulting in extremely long distances for axon regeneration to distal tar gets (e.g., hand, foot). Despite significant efforts, PNI repair has not progressed past nerve guidance tubes (NGTs) for the Dec. 10, 2015.

Surgical intervention is required if there is to be any prospect of repairing severed peripheral nerves. One surgical technique for attempting growth of a peripheral nerve involves providing a scaffold, usually in the form of a conduit, at the site of the nerve damage, to facilitate and encourage the extension of regenerating axons. Specifically, the scaffold is selected to provide an environment that will encourage nerve growth so that nerve function can be returned. To date, success rates for peripheral nerve growth have been low and it is presently not possible to achieve the extent of peripheral nerve growth that would be required in order to repair many of the injuries experienced by peripheral nerves.

When fabricating the next generation of nerve conduits, several aspects need to be considered. These include the biocompatibility of the materials, and the customized mechanical and degradation properties. Single-channel collagen conduits that possess a mechanical strength and are easy to process have previously been used in nerve regeneration applications.

A number of nerve conduits are FDA approved for relatively short nerve defects, such as Integra Neurosciences Type I collagen tube, NeuraGen™, Collagen Matrix Inc.'s neuroflex and Synovis Surgical Innovations Gem Neurptube™. These are single-channel tubes which are used only for small defects of several millimeters and do not address larger peripheral nerve injuries. In addition, axons regenerating across these single lumen tubes assume a dispersed direction, resulting in inappropriate target re-enervation and the co-contraction of opposing muscles or synkinesis.

In spite of the evolution of the surgical microscope and a prodigious effort into refining techniques for accurate nerve approximation, the clinical results of surgical nerve repair are still disappointing. Scar tissue resulting from the surgical manipulations required for direct proximal-to-distal nerve suture frequently interferes with the growth of proximal stump axons into the distal nerve stump. If a substantial number of axons are prevented from crossing the anastomotic site, neuroma (painful nerve cell tumor) formation often results. As a result, prospects for achieving significant reinnervation are reduced. The end result is a lack of full return of motor and/or sensory function.

Additionally, the regenerative potential of the damaged proximal nerve is frequently unpredictable and poorly understood. Severe nerve injuries have required microsurgical grafting to span a defect. This technique involves surgically grafting a piece of a nerve, from another part of the body, this approach too has certain limitations. The area from which the nerve was removed is left without sensation. Moreover, the amount of nerve tissue that can reasonably be removed for such grafts is also limited. However, suture techniques and/or grafting have not always been sufficient for repair of a severe defect. Still further, suture under tension, gap reduction by stretching, mobilization, flexion of a joint, or rerouting may compromise sensitive intraneuronal vascularity, and autografts induce a second surgical site with requisite risks and complications.

Moreover, in many instances, there was either no nerve growth or only growth of connective tissue. Thus, the functional results of surgical repair of peripheral nerve injuries have been disappointing in spite of improved surgical techniques. Strategies have been devised for allegedly enhancing the regeneration of peripheral nerves (those outside the spinal cord and brain). Thus, protection of the site of a neurorrhaphy from infiltration with fibrous tissue and prevention of neuromatous formation by the use. of wrappers, cuffs, or tubes of various materials have been practiced since 1980. At that time, it was attempted to interpose a drain of decalcified bone between the severed ends of a sciatic nerve. Fibrous union without return of function, however, generally resulted. In addition to decalcified bone and vessels, fascialata, fat, muscle, parchment, Cargile membrane, gelatin, agar, rubber, fibrin film, and various metals have been used with varying degrees of success. Many materials failed because they incited a foreign body reaction, produced constricting scar tissue, were technically difficult to apply, or required secondary operation for their removal. Various enhancements in both end tubulation and nerve wrapping have continued in order to facilitate nerve repair.

Both biodegradable and non-resorbable materials have been used to act as a channel to promote growth and regeneration in severed nerves which have been sutured together or in connection with nerve grafts.

Although improved results in nerve regeneration have been obtained through the use of tubes filled with nerve regenerating promoters, there is still much room for further improvement. Particularly, the manufacture of tubes filled with such promoting agents is a relatively expensive and tedious process. Moreover, it would still be desirable to provide a means by which an even greater number of myelinated axons are regenerated, a faster rate of nerve growth is achieved, and longer nerve gaps are spanned. A need still exists to fulfill such a need and still reduce or eliminate problems that have been encountered with prior art nerve repair attempts such as revascularization, excessive fibrosis, reorientation of nerve fibres, and the final poor return of function of the end organs.

Bridging of Small gaps or come close to matching the performance of autografts. As a result, the field is in desperate need of a transformative technology for repair of peripheral nerve injury. The key failing of all current strategies to functionally repair major nerve trauma is the inability to coax a Sufficient number of axons to grow a Substantial distance to reinnervate distal targets (e.g., hand) and restore function. To overcome this failing, repair strategies must address two major challenges: (1) encourage rapid regeneration of proximal axons and (2) maintain the pro-regenerative capacity of the distal nerve segment for regenerating axons.

Degeneration of the axon segments distal to a nerve injury site is an inevitable consequence of transection of or injury to the nerve; however, the supporting Schwann cells in the distal nerve segment survive and switch to a pro-regenerative phenotype to support axon growth. This pro-regenerative phenotype includes a change in cellular alignment to form parallel columns, providing tracts that serve as guides for regenerating axons. Unfortunately, the natural pro-regenerative environment degrades after several months without the presence of axons, thus depriving regenerating axons of their "road map" to an end target. This occurs when the time it takes to regenerate axons to infiltrate the distal segment is greater than the time the Schwann cells can maintain their pro-regenerative phenotype. Often, following long or proximal PNI, the pro-regenerative environment fails and there is incomplete functional recovery. For example, a patient with a PNI of the upper arm may regain elbow, but not hand function, due to the distance between the nerve injury and the end targets in the hand, which are often not reached by proximal axons before the distal environment is no longer pro-regenerative. In another example, a PNI is not treatable due to the large size of the nerve lesion or injury, irrespective of the lesion or injury location.

Various techniques for prolonging the pro-regenerative capacity of the distal nerve segment following nerve injury have been explored. These include providing neurotrophic factors (e.g., GDNF, BDNF, and TGF-beta) to the distal nerve segment; administering electrical stimulation to the nerve sheath in an attempt to stimulate acceleration of axon regeneration; and transferring a foreign sensory nerve or an adjacent healthy nerve to the denervated nerve sheath. However, such techniques are often limited by a lack of efficacy, particularly with regard to long-term efficacy.

In addition, some of these techniques have the clear disadvantage of transecting a healthy nearby nerve for the purpose of transferring it to the adjacent denervated nerve stump.

Thus, there is a need in the art for more effective means of maintaining the pro-regenerative capacity of denervated distal nerve segments so that the effectiveness of current or future means of PNI repair can be increased. There is a particular need in the art for maintaining pro-regenerative capacity and alignment of Schwann cells in the denervated distal nerve segment in long-term.

At present, support cells used in the tissue engineered nerves include Schwann cells and various stem cells, which are allogeneic cells, and may cause immunogenicity, which is not suitable for clinical applications. On the other hand, the in vivo fate and biological effects of support cells after they are implanted into the body are not fully clear, and they may be inactivated in the environment of the body, thus failing to achieve expected biological effects. All the above issues limit the development of tissue engineered nerve grafts.

Nerve damage in patients will often not regenerate naturally, and can lead to permanent loss of sensitivity and function. For this reason, surgical and therapeutic interventions to promote repair can be desirable.

Reference is made to GB2386841 titled Multi-channel bioresorbable nerve regeneration conduit and process for preparing the same, by applicant IND TECH RES INST. This invention describes a multi-channel bioresorbable nerve regeneration conduit having a hollow round tube of porous bioresorbable polymer and a multi-channel filler made from a porous bioresorbable polymer film located inside the tube.

Reference is made to U.S. Pat. No. 5,019,087, titled nerve regeneration conduit, by applicant American Biomaterials Corp. The invention discloses a method of spinning a collagen and laminin mixture onto a mandrel to make a single channel nerve conduit.

Reference is made to U.S. Pat. No. 3,786,817, titled METHOD AND APPARATUS FOR AIDING SEVERED NERVES TO JOIN, by applicant PALMA J. The invention describes the use of a non-resorbable tube to aid in the alignment and joining of severed nerves. Here, the ends of a severed nerve are inserted into the ends of a tube until the nerve ends are close to each other or touch each other at the center of the tube. A fluid such as nitrogen is passed though the tube to aid in regeneration.

Reference is made to In U.S. Pat. No. 4,534,349, titled ABSORBABLE SUTURELESS NERVE REPAIR DEVICE, by applicant 3M Co. The invention is an absorbable hollow tubular device. Which allegedly enables the sutureless repair of lacerated, severed, or grafted nerves wherein the device is comprised of a body-absorbable polymer.

Reference is made to CN1589913, entitled A tissue engineering peripheral nerve used for repairing peripheral nerve defect and its preparation method, by applicant School of Stomatology, Fourth Military Medical University of Chinese People's Liberation Army. The invention describes a tissue engineered nerve used for repairing peripheral nerve defect. The tissue engineered nerve consists of a nerve conduit made of biodegradable materials added with glial cells or stem cells having ability to differentiate into glial cells, which are used as seed cells, and modified with microspheres for controlled release of neurotrophic factors and with ECM molecules.

Reference is made to WO2004/087231, titled self-aligning tissue growth, by applicant Ucl Biomedica Plc. The invention describes a self-aligning tissue growth guide. The guide comprises a core of a biopolymer matrix which is fixed to an outer sheath at two points. The core is seeded with cells, which generate a mechanical contractile force leading to self-alignment of the cells within the core. This produces a cellular guidance substrate for regenerating tissue in vivo. The tension in the core can also lead the fibres of the matrix to align. The combination of cellular alignment and substrate alignment serves to guide cellular regrowth in a subject. As described in WO2004/087231, the biopolymer matrix is preferably a collagen matrix. Cells used to seed the matrix align and contract but do not proliferate to form organized tissue. The list of cells given in the publication as being of use includes Schwann cells. An embodiment of the guide may also include cells from the tissue of interest seeded within the matrix, and which will grow and be guided by the contractile cells.

Another reference is made to 9123/DELNP/2014, titled Scaffold, by applicant THE UNIVERSITY OF SHEFFIELD. The invention provides a method for producing an electrospun scaffold, comprising electrospinning a polymer or co-polymer onto a template comprising a conductive collector having a three dimensional pattern thereon, wherein said electrospun polymer or co-polymer preferentially deposits onto said three dimensional pattern.

Another reference is made to 368/DELNP/2012, titled BIODEGDRADABLE SCAFFOLD FOR SOFT TISSUE REGENERATION AND USE THEREOF, by applicant COLOPLAST A/S. The present invention relates to new reinforced biodegradable scaffolds for soft tissue regeneration, as well as methods for support and for augmentation and regeneration of living tissue, wherein a reinforced biodegradable scaffold is used for the treatment of indications, where increased strength and stability is required besides the need for regeneration of living tissue within a patient. The present invention further relates to the use of scaffolds together with cells or tissue explants for soft tissue regeneration, such as in the treatment of a medical prolapse, such as rectal or pelvic organ prolapse, or hernia.

Another reference is made to 201821042296, titled PROCESS FOR PREPARATION OF TUBULAR GRAFTS OR TUBULAR SCAFFOLDS FOR TISSUE ENGINEERING, by applicant Dr. D. Y. Patil Vidyapeeth. The present invention relates to a process for preparing tubular grafts or tubular scaffolds for tissue engineering, which is amenable to automation, using which the manufacturing of tubular scaffolds or grafts derived from them can be scaled up. More particularly, the present invention further relates to a process for preparation of tubular grafts or tubular scaffolds, which are of uniform diameter, seamless in construction, and are free from tears and other defects arising due to the manufacturing process. The present invention also relates to a process for preparing tubular grafts or tubular scaffolds for tissue engineering, using a sacrificial mould and sacrificial mandrel approach, wherein a sacrificial mould is used for preparing a sacrificial mandrel. The present invention further relates to a process for preparing tubular grafts or tubular scaffolds for tissue engineering, wherein use of noncell friendly chemicals such as organic solvents is avoided.

Another reference is made to U.S. Pat. No. 10,507,187, titled Regenerative tissue grafts and methods of making same, by applicant Jackson; Wesley M. (Albany, CA), Nesti; Leon J. (Silver Spring, MD), Tuan; Rocky S. (Bethesda, MD The present invention discloses a graft containing a scaffold that includes a matrix in which are positioned mesenchymal progenitor cells (MPCs) has the capacity to substantially improve wound healing, including wounds resulting from injury to nerve, bone and vascular tissue. MPCs can be harvested from debrided muscle tissue following orthopaedic trauma. The traumatized muscle-derived progenitor cells are a readily available autologous cell source that can be utilized to effect or improve wound healing in a variety of therapeutic settings and vehicles.

However none of the inventions in prior art comprise novel and unique technique of culturing human mesenchymal stem cells, mesenchymal stem cells differentiated Schwann cells and nerve cells into a proliferating, sub-confluent layer on a biocompatible conduit/matrix prepared from plurality of composite polymers by using glutaraldehyde as a cross linker for direct implantation or delivery. In the present invention, the cells are transferred while in a proliferative state and the final product obtained is transported in semi-solid medium wherein the semi-solid medium is agar medium 1% to 3% and cell culture medium with essential growth factors. The agar medium contains HEPES 2-3 gm/l and sodium bicarbonate 2-3.5 gm/l. suitable for grafting and provides a better, efficient, easy to use, cost effective ready to use biodegradable and biocompatible artificial nerve conduit/matrix for nerve repair and regeneration with sensory and motor function in a synergistic manner. In the present invention, the grafts can be prepared within 12 days.

The present invention provides a novel and unique technique of nerve conduit/matrix preparation and culturing of human mesenchymal stem cells, schwann cells and neuronal cells and their proliferation on a biocompatible conduit/matrix suitable for nerve implantation/grafting. The invention provides a ready to use biodegradable and biocompatible tissue construct with autologous/allogeneic human stem cells based product. The present invention also provides a reconstructive procedure to meet the specific requirements necessary to achieve satisfactory healing of nerve injury and restore functional integrity in the least time and with the least complications and morbidity. The nerve conduit/matrix as provided by the present invention has tissue like properties and is capable of being used for nerve regeneration and repair in a synergistic manner.

OBJECTS OF THE INVENTION

The primary objective of the present invention is to provide artificial bioengineered nerve conduit/matrix for peripheral nerve injury.

Another objective of the present invention is to grow cells directly on the polymeric conduit/matrix (scaffold) for direct implantation or delivery.

Another objective of the present invention is to prepare grafts within 12 days.

Another objective of the present invention is to provide a ready to use biodegradable and biocompatible nerve conduit/matrix with autologous/allogeneic human stem cells-based product.

Another objective of the present invention is to provide a method of preparation of such device.

A further objective of the present invention is to develop artificial bioengineered nerve conduit/matrix for peripheral nerve injury, spinal cord injury and any other type of nerve injury repair and regeneration in a synergistic manner.

A further objective of the present invention is to develop artificial bioengineered nerve conduit/matrix for restoration of motor and sensory function of damaged or injured nerve.

SUMMARY OF THE INVENTION

The present invention provides a novel and unique technique of nerve conduit/matrix preparation and culturing of human mesenchymal stem cells, schwann cells and neuronal cells and their proliferation on a biocompatible conduit/matrix prepared from plurality of composite polymers by using glutaraldehyde as a crosslinker for direct implantation or delivery. In the present invention, the cells are transferred while in a proliferative state and the final product obtained is transported in semi-solid medium wherein the semi-solid medium is agar medium 1% to 3% and cell culture medium with essential growth factors. The agar medium contains HEPES 2-3 gm/l and sodium bicarbonate 2-3.5 gm/l suitable for grafting. The present invention provides a ready to use biodegradable and biocompatible tissue construct with autologous/allogeneic human stem cells-based product. The present invention also provides a reconstructive procedure to meet the specific requirements necessary to achieve satisfactory healing of nerve injury and restore functional integrity in the least time and with the least complications and morbidity. The nerve conduit/matrix as provided by the present invention has tissue like properties and is capable of being used for nerve regeneration and repair in a synergistic manner. In the present invention, the grafts can be prepared within 12 days.

STATEMENT OF THE INVENTION

Figure 1:
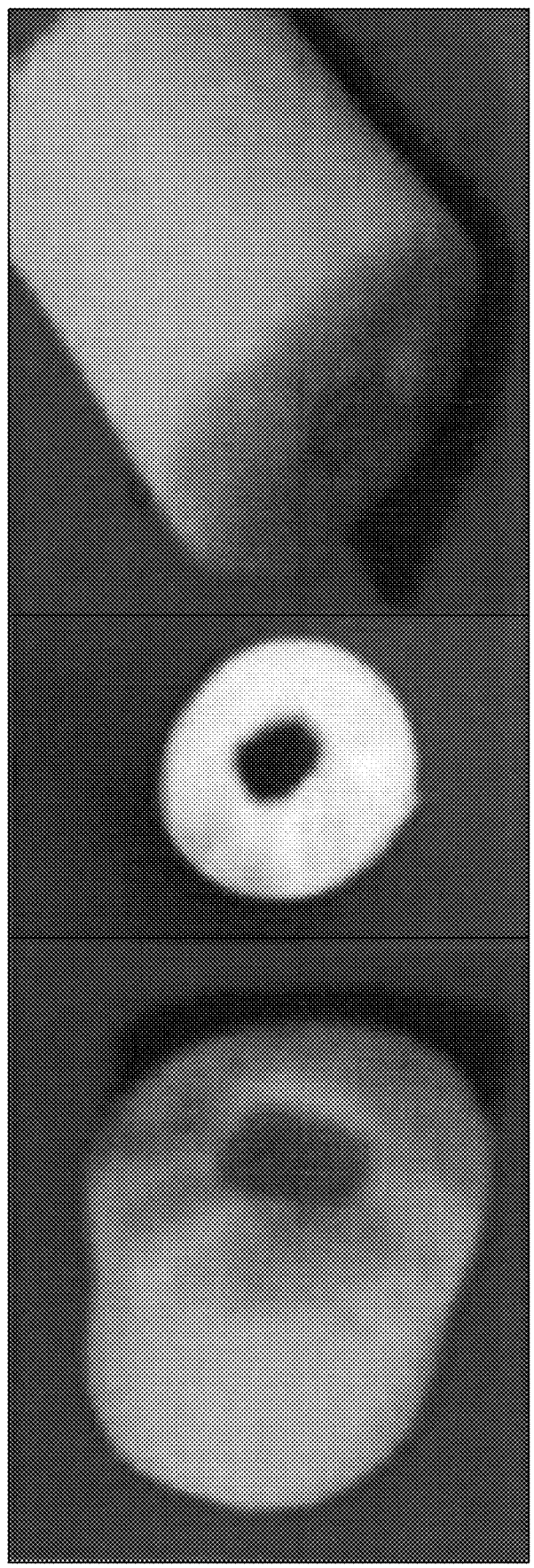
FIG. 1 shows the Design and fabrication of biopolymer-based nerve guidance Nerve conduit/Matrix Form.

Accordingly, the present invention provides novel and unique technique of culturing human mesenchymal stem cells, mesenchymal stem cells differentiated schwann cells and nerve cells into a proliferating, sub-confluent layer on a lyophilized biocompatible conduit/matrix prepared from plurality of composite polymers by using glutaraldehyde as a cross-linker without any integrated harmful chemicals for direct implantation or delivery of the said human mesenchymal stem cells, wherein in the said invention, the said cells are transferred while in a proliferative state and the final product obtained is transported in semi-solid medium. The said semi-solid medium is agar medium 1% to 3% and cell culture medium with essential growth factors including HEPES 2-3 gm/l and sodium bicarbonate 2-3.5 gm/l. suitable for grafting and provides a better, efficient, easy to use, cost effective ready to use biodegradable and biocompatible artificial nerve conduit/matrix for nerve repair and regeneration with sensory and motor function in a synergistic manner wherein the grafts can be prepared within 12 days.

DETAILED DESCRIPTION OF THE INVENTION

It should be noted that the particular description and embodiments set forth in the specification below are merely exemplary of the wide variety and arrangement of instructions which can be employed with the present invention. The present invention may be embodied in other specific forms without departing from the spirit or essential characteristics thereof. All the features disclosed in this specification may be replaced by similar other or alternative features performing similar or same or equivalent purposes. Thus, unless expressly stated otherwise, they all are within the scope of present invention. Various modifications or substitutions are also possible without departing from the scope or spirit of the present invention. Therefore it is to be understood that this specification has been described by way of the most preferred embodiments and for the purposes of illustration and not limitation.

The present invention provides a novel and unique technique of nerve conduit/matrix preparation and culturing of human mesenchymal stem cells, schwann cells and neuronal cells and their proliferation on a biocompatible conduit/matrix suitable for nerve implantation/grafting.

The present invention provides a ready to use biodegradable and biocompatible tissue construct with autologous/allogeneic human stem cells based product.

The present invention also provides a reconstructive procedure to meet the specific requirements necessary to achieve satisfactory healing of nerve injury and restore functional integrity in the least time and with the least complications and morbidity. The nerve conduit/matrix as provided by the present invention has tissue like properties and is capable of being used for nerve regeneration and repair.

The present invention is directed to bioengineered tissue constructs of cultured cells and endogenously produced extracellular matrix components without the requirement of exogenous matrix components or network support or scaffold members. The invention can thus advantageously be made entirely from human cells, and human matrix components produced by those cells, for example, when the bioengineered tissue construct is designed for use in humans.

The present invention is also directed to methods for producing tissue constructs by stimulation of cells in culture, such as Mesenchymal stem cells, and Mesenchymal stem cells differentiated into schwann cells and nerve cells to produce extracellular matrix components without the addition of either exogenous matrix components, network support, or scaffold members to helpful in nerve repair and regeneration.

In the present invention, further, this tissue construct can be made by seedings of Mesenchymal stem cells and Mesenchymal stem cells differentiated schwann cells and nerve cells to produce a cultured tissue construct that mimics the cell composition and tissue structures for signal transduction, nerve repair and regeneration as native tissues. The tissue constructs of the invention are useful for clinical purposes such as nerve grafting to a patient with tissue or organ defect, such as peripheral nerve injury or any other type of nerve injury, or for in vitro tissue testing or animal grafting such as for safety testing or validation of pharmaceutical, cosmetic, and chemical products.

The present invention uses proliferative/preconfluent Mesenchymal stem cells (MSCs), schwann cells, nerve cells, mesenchymal stem cells differentiated schwann cells and mesenchymal stem cells differentiated neuronal cells whereby cells are transferred from culture to the ready to use living nerve conduit/matrix.

In an embodiment, the cells are grown directly on the polymeric conduit/matrix (scaffold) for direct implantation or delivery. The cells with scaffold can therefore be transferred as such to the patient thus avoiding the potential damage occurring in the conventional enzymatic separation from the culture vessel.

In an embodiment, the cells are transferred while in a proliferative state. In some embodiments, the use of preconfluent cells aids in the adherence of such cells to the application site as they express an integrin profile different from fully differentiated, terminal cells.

In an embodiment, the interactive component of the invention is provided by the use of actively proliferating Mesenchymal stem cells, schwann cells, nerve cells (unipolar or bipolar or multipolar). During nerve repair and regeneration of damaged nerve, a number of cytokines, growth factors etc. are released at the application site, that will helpful in signal transduction and nerve regeneration.

In an embodiment, the cells at the application site express molecules that have both an autocrine as well as a paracrine effect.

In an embodiment, the uses of an artificial nerve conduit graft substitute are useful for both repair and regeneration of damaged nerve in a synergistic manner. Repair indicates the process that a tissue undergoes to completely regenerate/reform. Allogeneic Mesenchymal stem cells, Schwann cells and nerve cells used in this nerve conduit/matrix will helpful in repair and regeneration of the damaged nerve.

In another embodiment, the process involves the optimization of scaffolds onto which cells are seeded to form a uniform tissue with scaffolds that provide physical and chemical cues to guide the process. Scaffolds may be selected from a group comprising of natural biopolymers such as chitosan, gelatin, collagen and hyaluronic acid.

In another embodiment, the Scaffolds take forms ranging from sponge like sheets to gels to highly complex structures with intricate pores and channels made with new materials processing technologies. The spatial and compositional properties of the scaffold, the porosity of the scaffold and interconnectivity of the pores are all required to enable cell penetration into the structure as well as the transport of nutrients and waste products. Differential porosity will helpful in the cells attachment and signal transduction.

In an embodiment, the sequential timed patterned physico-chemical treatment of the four or more polymers is carried on to get lyophilized 3D scaffold of polyelectrolyte complex (PEC) and also at the same time using a specifically designed aspect ratio of a system for agitation/homogenization. The sequential timed patterned physico-chemical treatment of polymers can be as dissolution of gelatin at temperature 35-75° C., preferably at 60° C. using 5% of gelatin, wherein the process comprises:

Stirring of the gelatin solution at 2000-3200 rpm at temp 15-30° C. for 15-25 min.
  a) Adding of 1% chitosan solution (in 0.5-2.5% glacial acetic acid solution) dropwise in gelatin solution at temp 15-30° C. and stir the solution with homogenizer for 20-30 min.
  b) Adding of hyaluronic solution (in milli Q water) preferably 0.1-1% dropwise in mixture and stir for 10 minutes.
  c) Adding of collagen solution type 1 or type 4 (in glacial acetic acid solution) preferably 0.1-1% dropwise in mixture and stir for 10 minutes.
  d) Adding of glutaldehyde solution preferably 25-50% dropwise at final concentration of 0.1-0.5%.

In an embodiment, once the above method of physico-chemical treatment of polymers is complete then the process of freeze drying of the composite solution is carried on. The composite was freeze at −80° C. for 12 hrs and then lyophilize for 72 hrs at 0° C. and 500 motor vacuum.

In an embodiment, after freeze drying conduit/matrix was neutralized with ammonia fumes (25% ammonia solution fumes) for 12 hrs in closed chamber inside the fume hood.

In an embodiment, further mesenchymal stem cells, schwann cells and nerve cells are seeded onto biocompatible scaffold at cell density of $0.5 \times 10^5$ to $0.8 \times 10^5$ cell/cm$^2$. The cells are monolayer and 80% to 100% confluent at the final stage of product formulation. The cells used for seeding is passage 2 to passage 5. The mesenchymal stem cell, schwann cells and nerve cells used for seeding is human mesenchymal stem cells, schwann cells is differentiated from human mesenchymal stem cells and nerve cells is differentiated from human mesenchymal stem cells and only pure population. The mesenchymal stem cells, schwann cells and nerve cells have secrete several growth factors and cytokines (extracellular matrix) helpful in nerve repair and regeneration.

In an embodiment, the final product obtained will transport in semi-solid medium. The semi-solid medium is agar medium 1% to 3% and cell culture medium with essential growth factors. The agar medium contains HEPES 2-3 gm/l and sodium bicarbonate 2-3.5 gm/l. The semi-solid medium contains agar medium and cell culture medium in the ratio of 5:5, 6:4, 7:3 and 8:2 or any one of them respectively. The semi-solid medium maintains the cell viability of matrix between 60% to 90% at the temperature 4° C. to 37° C. for 28 days.

EXAMPLES

The following examples are for the purposes of illustration only and therefore should not be construed to limit the scope of the invention:

Example 1: Design and Fabrication of Biopolymer-Based Nerve Guidance Conduit/Matrix Preparation of the Nerve Conduit/Matrix:

In an embodiment, take 50 ml of 5% gelatin solution and homogenize it for 15 min at 2000 rpm. Add 25 ml of 1% chitosan solution dropwise into the gelatin solution. Continue stir this mixture for 30 min to form a homogenous blend. Dropwise add 500 µl of 0.1% HA solution with stirring for 10 min. To this blend, add 1 ml of 0.1% collagen solution. After 10 min of continuous stirring, add 200 µl of 50% glutaraldehyde solution for crosslinking. Once the mixture is homogenized cast sample in trays/conduits and freeze it down at −80° C. for 12 hr followed by lyophilization (cycle 72 hrs, drying at 0° C., vacuum 500 mtorr) to form porous scaffolds.

Mesenchymal Stem Cells, Schwann Cells and Nerve Cells Inoculation and their Culture:

In an embodiment, $0.5 \times 10^5$ cells were seeded in the pre acclimatized scaffold (scaffold soaked in cell culture medium) and culture the cells at the day 12-15. After/between the day 12-15 scaffolds were completely filled with mesenchymal stem cells, schwann cells and nerve cells and rich of growth factors and nutrients as shown in FIG. 1.

Example 2: In Vitro Degradation Behavior of Nerve Conduit/Matrix

In an embodiment, the in vitro degradation of Nerve conduit/Matrix was studied by incubating them in an enzymatic solution and then monitoring their weight-losses at different time points.

In an embodiment, Scaffold samples were incubated in 1×PBS containing trypsin (0.25 mg/ml) & collagenase (0.1 mg/ml) at 37° C. in a shaker incubator at 60 rpm for various periods of up to 21 days.

In an embodiment, at predetermined time intervals, the scaffolds were removed from the incubation medium, washed with deionized water, then subsequently oven dry for final weight measurement. Weight-loss was then determined as a difference between dry mass of sample before and after the incubation, normalized to dry mass of sample before the incubation.

In an embodiment, Scaffolds incubated in trypsin had the highest weight reduction after two weeks of incubation compared to incubation in collagenase. In addition, in vitro degradation of scaffolds in PBS, saline and media at 37° C. was also performed to check long term mechanical stability and degradation of scaffold material.

Figure 2:
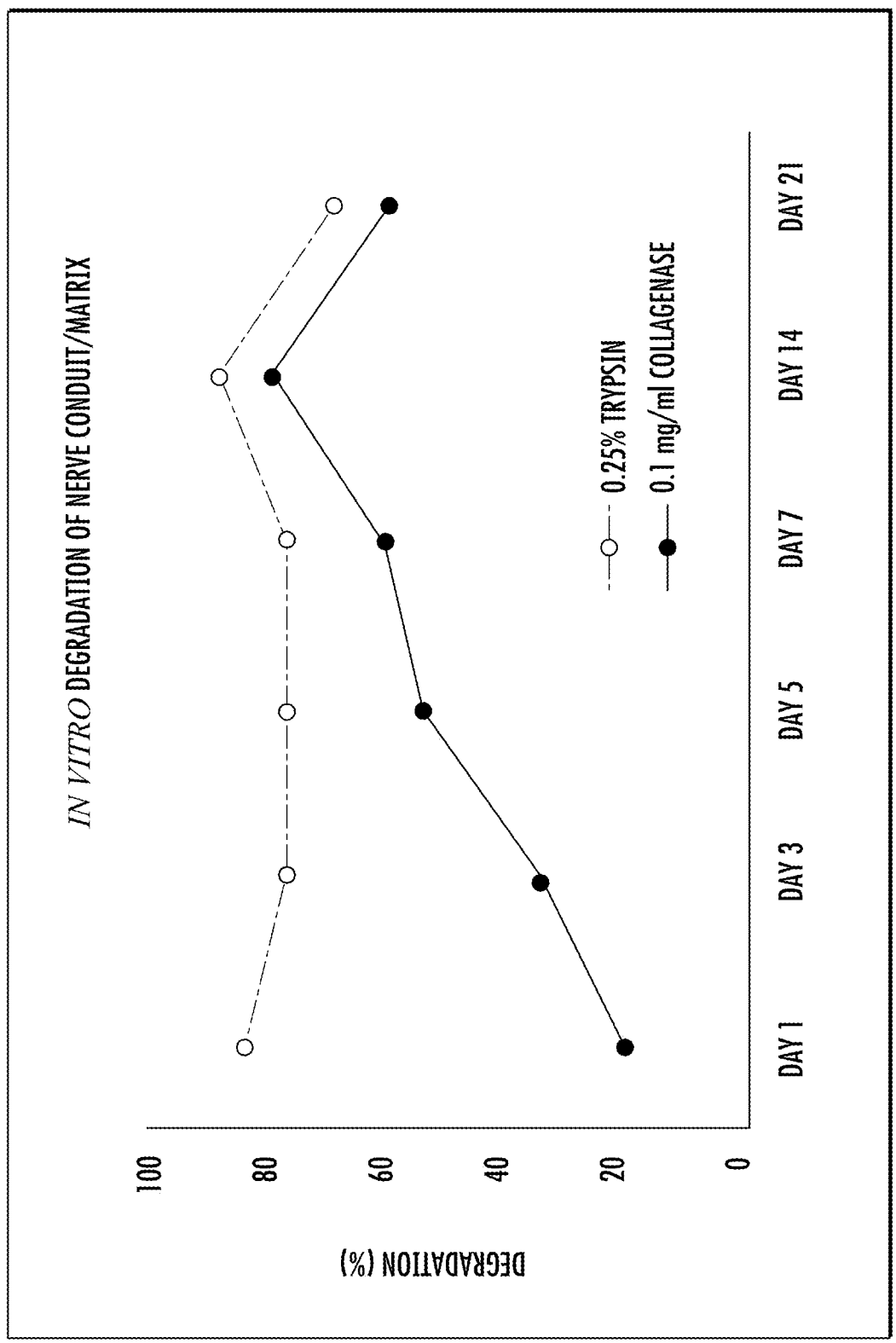
FIG. 2 shows Degradation behavior of Nerve conduit/Matrix in Trypsin and collagenase.

In an embodiment, Scaffolds were not degraded in PBS, saline and media up to four months indicating controlled degradation behavior of nerve conduit/matrix as depicted in FIG. 2.

Example 3: Swelling Test of Fabricated Nerve Conduit/Matrix

Figure 3:
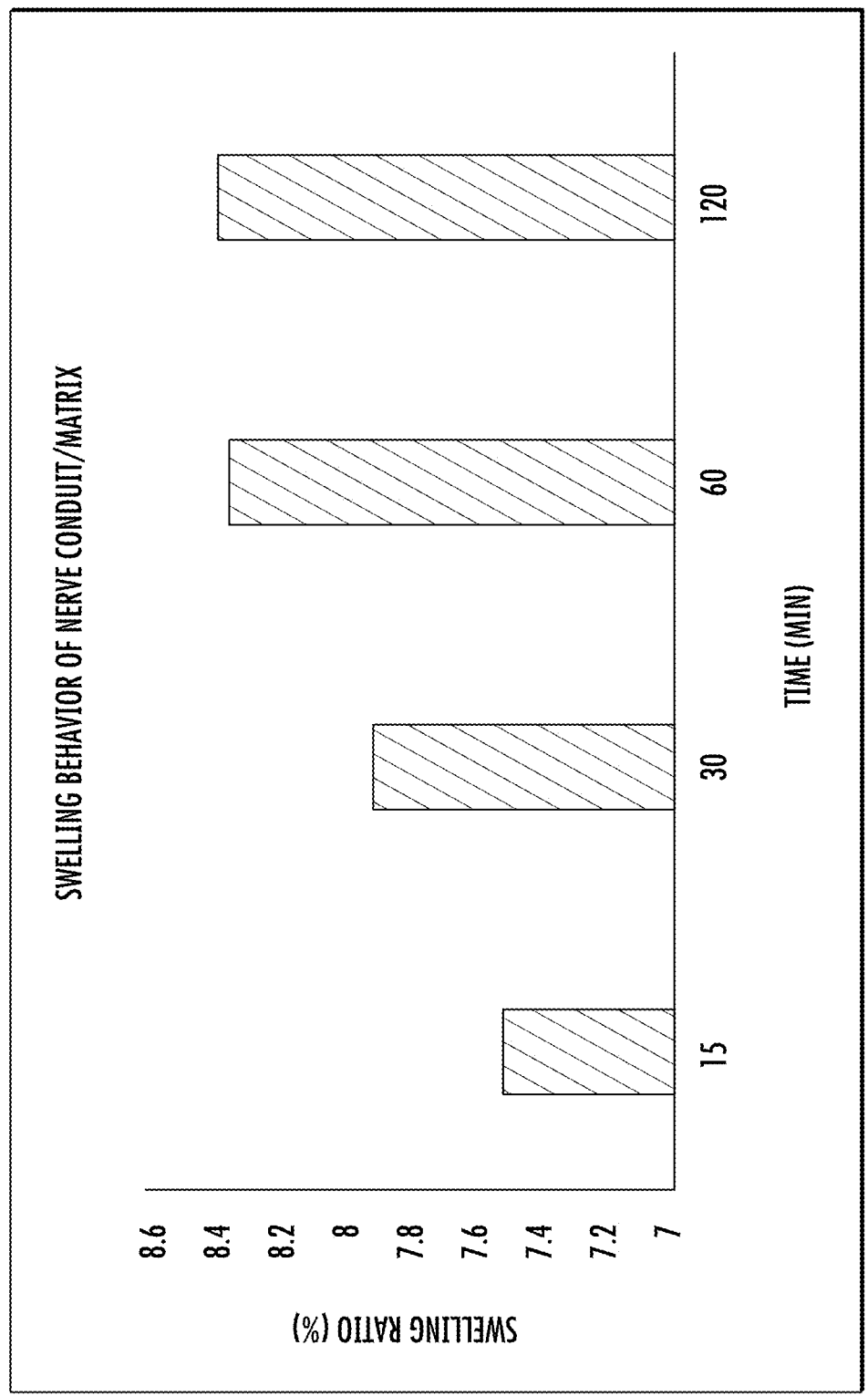
FIG. 3 shows Swelling ratio of Nerve conduit/Matrix in 1×PBS.

In an embodiment, to determine the percentage of water absorption, swelling studies were performed by immersion of scaffolds in 1×PBS. The dry weight of the scaffold was determined before immersion (Wd). Scaffolds were placed in PBS buffer solution and after a predetermined time points, the scaffolds were taken out and surface adsorbed water was removed by filter paper and their wet weight were recorded (Ww) as disclosed in FIG. 3. The ratio of swelling was determined using equation:

$$\text{Swelling ratio} = \frac{(Ww - Wd)}{Wd}$$

Example 4: Fourier Transform Infrared (FTIR) Analysis

Figure 4:
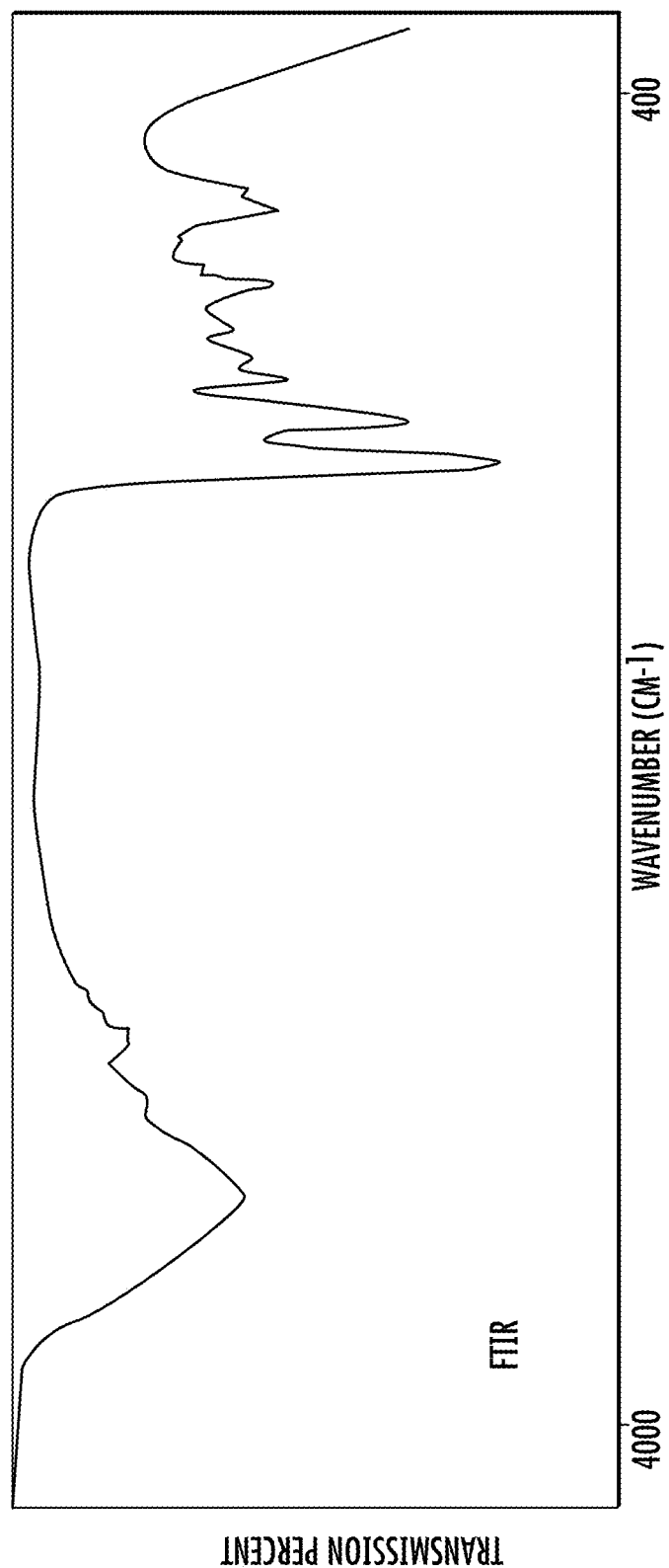
FIG. 4 shows the FTIR spectra of glutaraldehyde cross-linked nerve conduit/matrix.

In an embodiment, the chemical structure of the fabricated Nerve conduit/Matrix was analyzed by Fourier transform infrared spectroscopy (FTIR). The infrared spectra of the scaffold was measured over a wavelength range of 4000-400 cm$^{-1}$ as disclosed in FIG. 4.

Example 5: Morphological Characterization of Nerve Conduit/Matrix Using SEM

Figure 5:
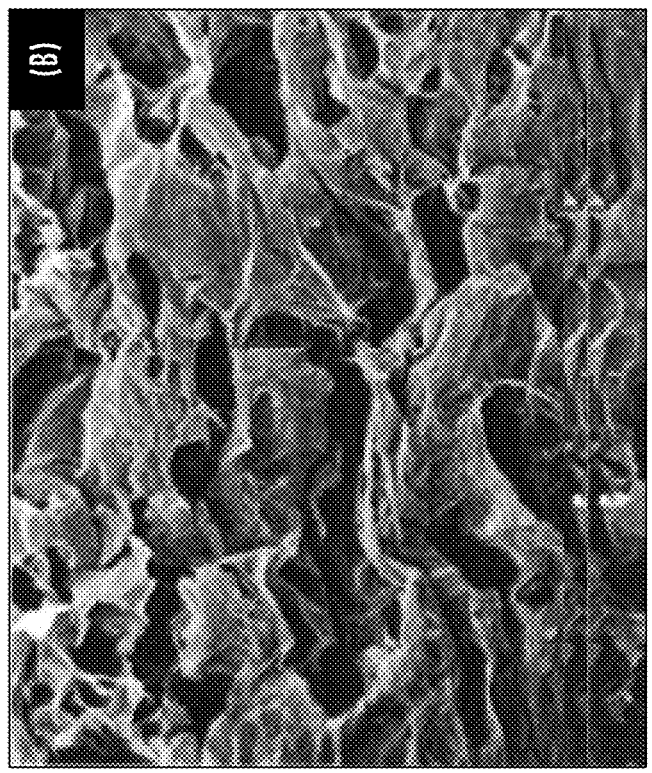
FIG. 5 shows Surface morphology of Nerve conduit/Matrix by SEM analysis (A) Cross-sectional view (100×) and (B) Surface view (200×).
Figure 5:
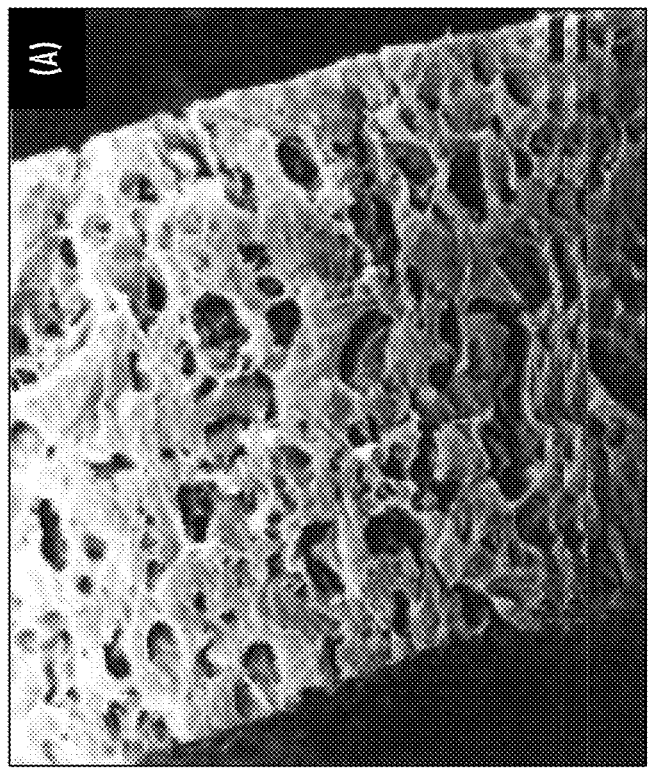

In an embodiment, scanning electron microscopy (SEM) was performed to study the surface and cross-sectional morphology of nerve conduit/matrix. The SEM image (FIG. 5) showed that the nerve conduit/matrix possessed a well-defined and well integrated porous structure that is essential for cell attachment, proliferation and survival. The images at higher magnification indicate the presence of open and interconnected pores of different sizes on the surface of scaffolds. Thus, nerve conduit/matrix possess sufficient porous morphology beneficial for vascularization and nutrient exchange between the lumen and the outer environment.

Example 6: Evaluation of Nerve Conduit/Matrix Cytotoxicity by MTT Assay

In an embodiment, in vitro cytotoxicity assays were performed to test the biocompatibility of nerve conduit/ matrix. This assay is based on the measurement of viability of cells via metabolic activity. Yellow water-soluble MTT (3-(4,5-dimethylthiazol-2-yl)-2,5-diphenyltetrazoliumbromid) is metabolically reduced in viable cells to a blue-violet insoluble formazan. The number of viable cells correlates to the colour intensity determined by photometric measurements after dissolving the formazan in DMSO. The cytotoxicity of the scaffolds was evaluated according to ISO guidelines 10993-5-2009, using 24 hr extraction period at dynamic condition.

To calculate the reduction of viability compared to the blank, following equation was used:

$$\% \text{ Viability} = \frac{\text{Absorbance Extract Concentration (570 nm)}}{\text{Absorbance Blank (570 nm)}}$$

Figure 6:
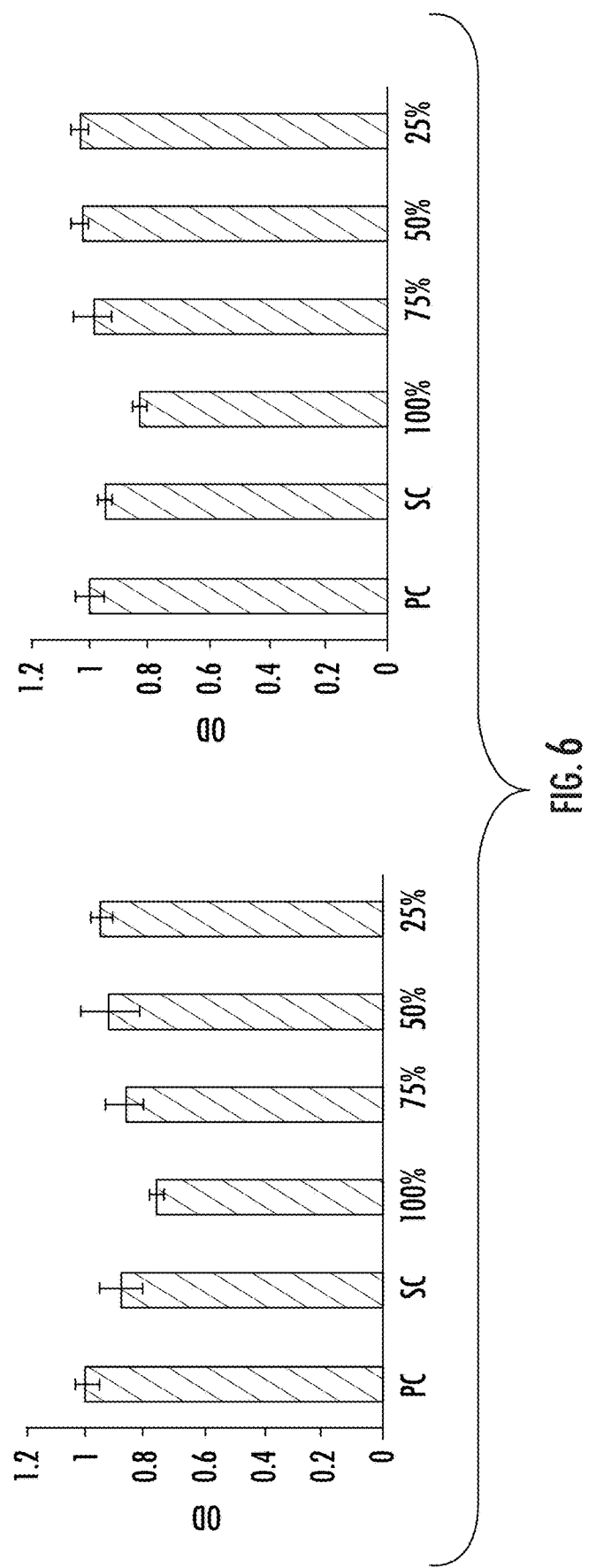
FIG. 6 shows MTT assay showing the biocompatibility of Nerve conduit/Matrix with L929 cells. (PC-plain control; SC-static control; DC-dynamic control).

Clearly, MTT data (FIG. 6) revealed that scaffold nerve conduit/matrix did not induce any cytotoxic response at any of the tested extract concentrations. Overall, nerve conduit/matrix displayed significant biocompatibility and cell viability to L929 cells.

Figure 7:
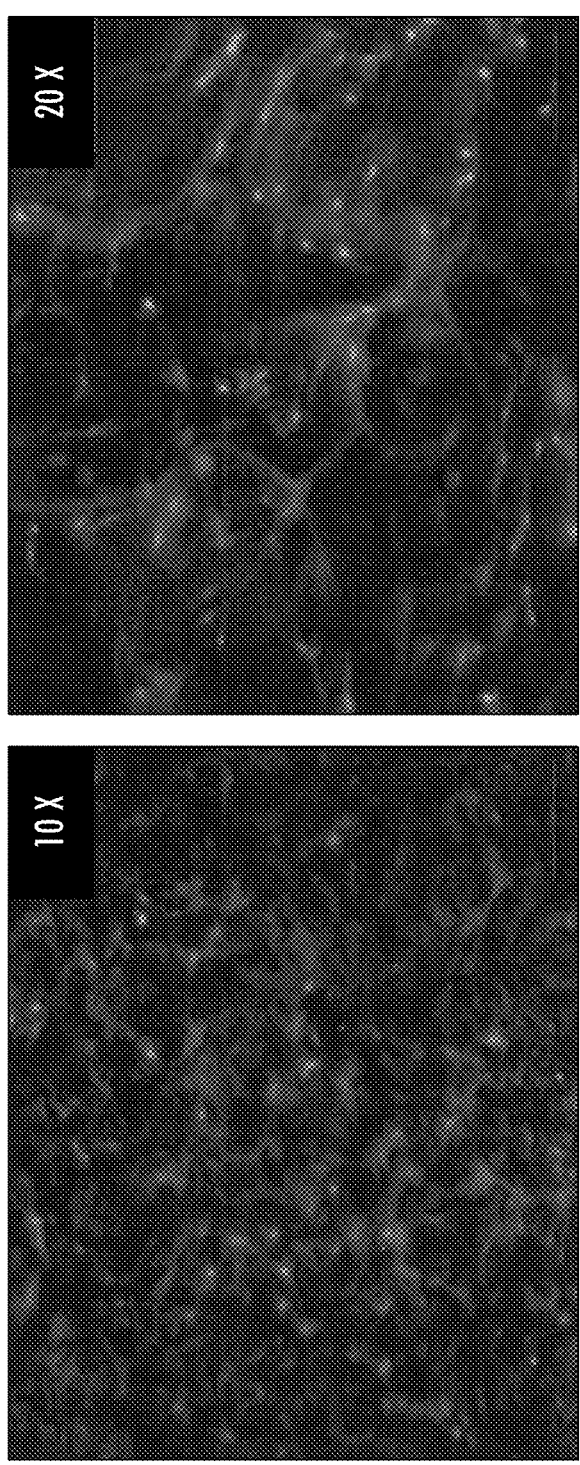
FIG. 7 shows Fluorescence images showing viability of MSCs on Nerve conduit/Matrix on day 7 in culture.

Example 7: Evaluation of Cell Attachment and Proliferation of MSCs on Nerve Conduit/Matrix In an embodiment, calcein-AM staining was performed to check the nerve conduit/matrix support for cell adhesion and proliferation of MSCs. Sterile scaffold was equilibrated it in culture medium overnight before seeding. MSCs were seeded at a density of $5 \times 10^4$ cells per scaffold followed by incubation at 37° C. in a $CO_2$ incubator. After 5 days of culture, media was removed from scaffold and washed with serum free media to completely remove the serum esterase activity. 2 µM Calcein-AM staining solution was prepared by adding 1 µl of 2 mM Calcein-AM to 1 ml of serum free media. Sufficient volume of Calcein-AM staining solution was added to cover the scaffold surface. Cells were incubated for 30 min at 37° C. Labeled cells were imaged using fluorescence microscopy to check cell adhesion & proliferation as disclosed in FIG. 7.

Example 8: PKH26 Staining of MSCs on Nerve Conduit/Matrix

Figure 8:
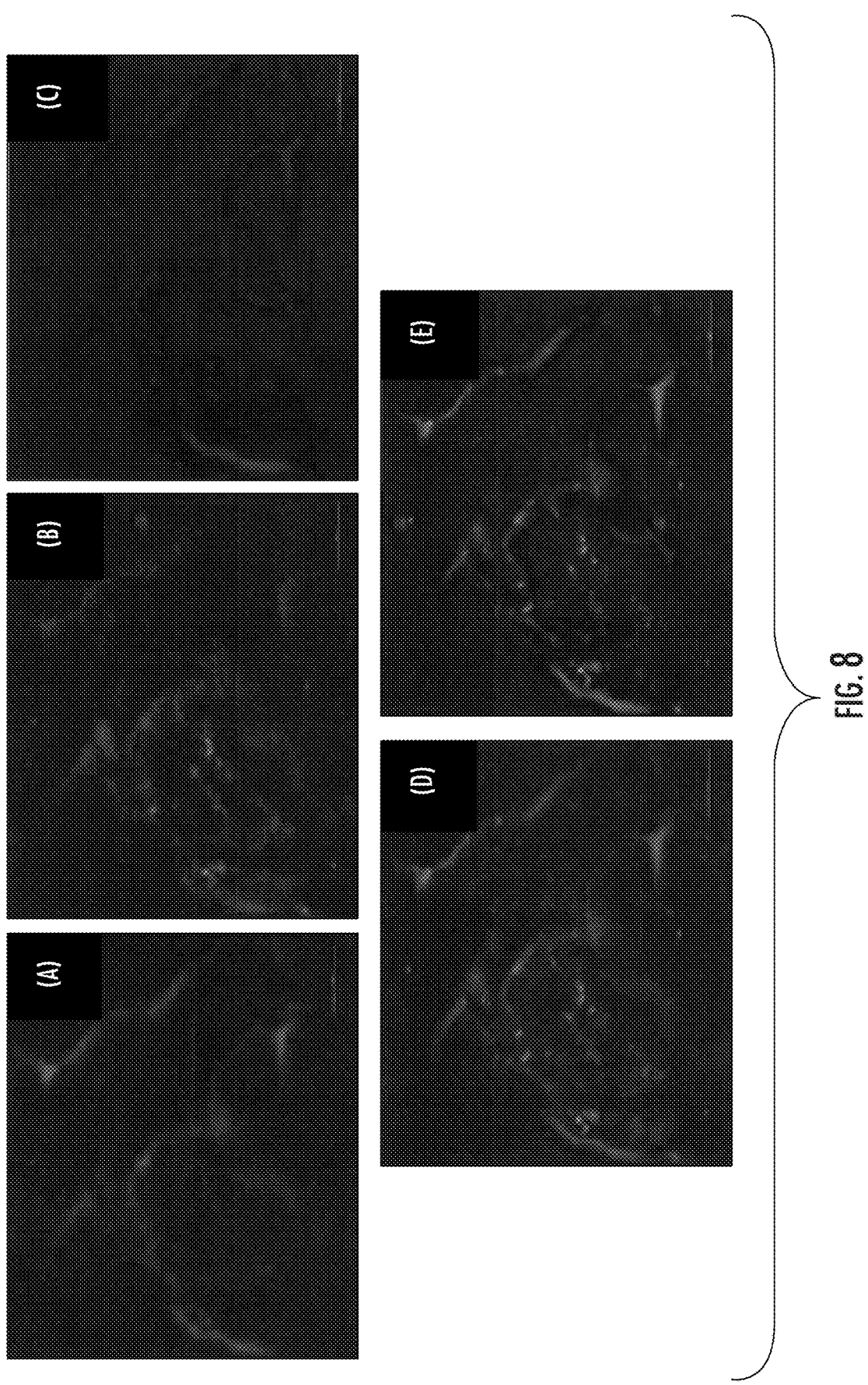
FIG. 8 shows Biocompatibility of Nerve conduit/Matrix for MSCs. (A) MSCs pre-stained with PKH26 growing uniformly across the scaffold; (B) Calcein-AM stained MSCs on nerve conduit/matrix scaffold; (C) Nuclear DAPI stained; (D) Merge PKH and DAPI; (E) Merge PKH, DAPI and Calcein-AM (10× magnification).

In an embodiment, PKH26 staining was performed to track the labelled MSCs on nerve conduit/matrix after 48 hrs of culture. MSCs pre-stained with PKH26 grown uniformly across the scaffold and exhibits adequate fluorescent signal after 48 hrs in culture. Calcein staining further confirmed the biocompatibility of scaffold nerve conduit/matrix for MSCs as disclosed in FIG. 8.

Example 9: Morphological Observation of Cell Adhesion Through SEM

Figure 9:
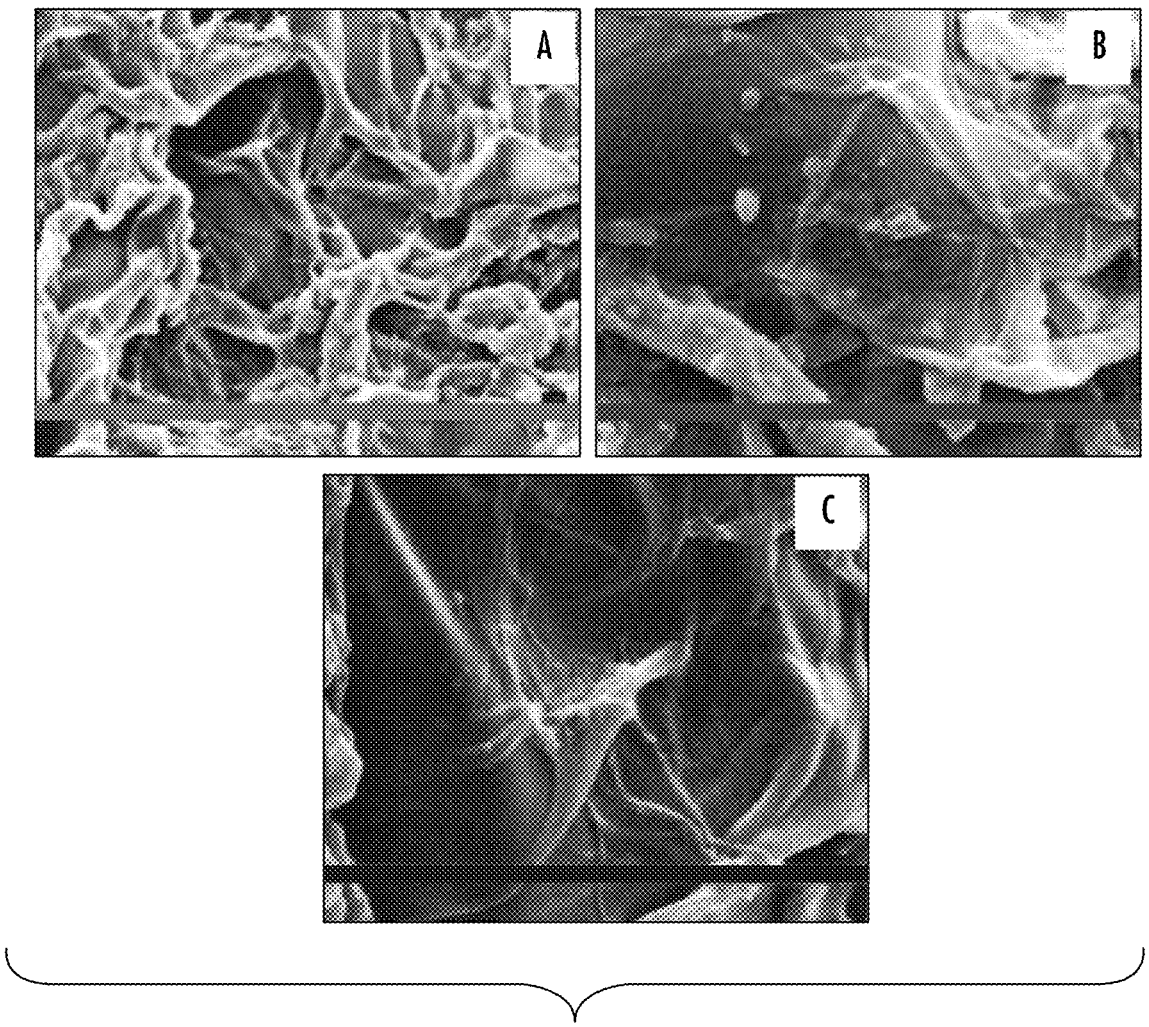
FIG. 9 shows Scanning electron micrographs of MSCs seeded on the surface of Nerve conduit/Matrix.

In an embodiment, MSCs were cultured at the concentration of $0.5 \times 10^5$ cells on nerve conduit/matrix scaffold. After 5 days of cell culture, the morphology of cells seeded on the composite scaffolds was observed using SEM. As shown in FIG. 9, the MSCs were well attached and spread out, showing more cell outgrowths. In addition, cell invasion indicates the porous nature of conduit, which provides enough space and 3D environment for cell growth and migration.

Figure 10:
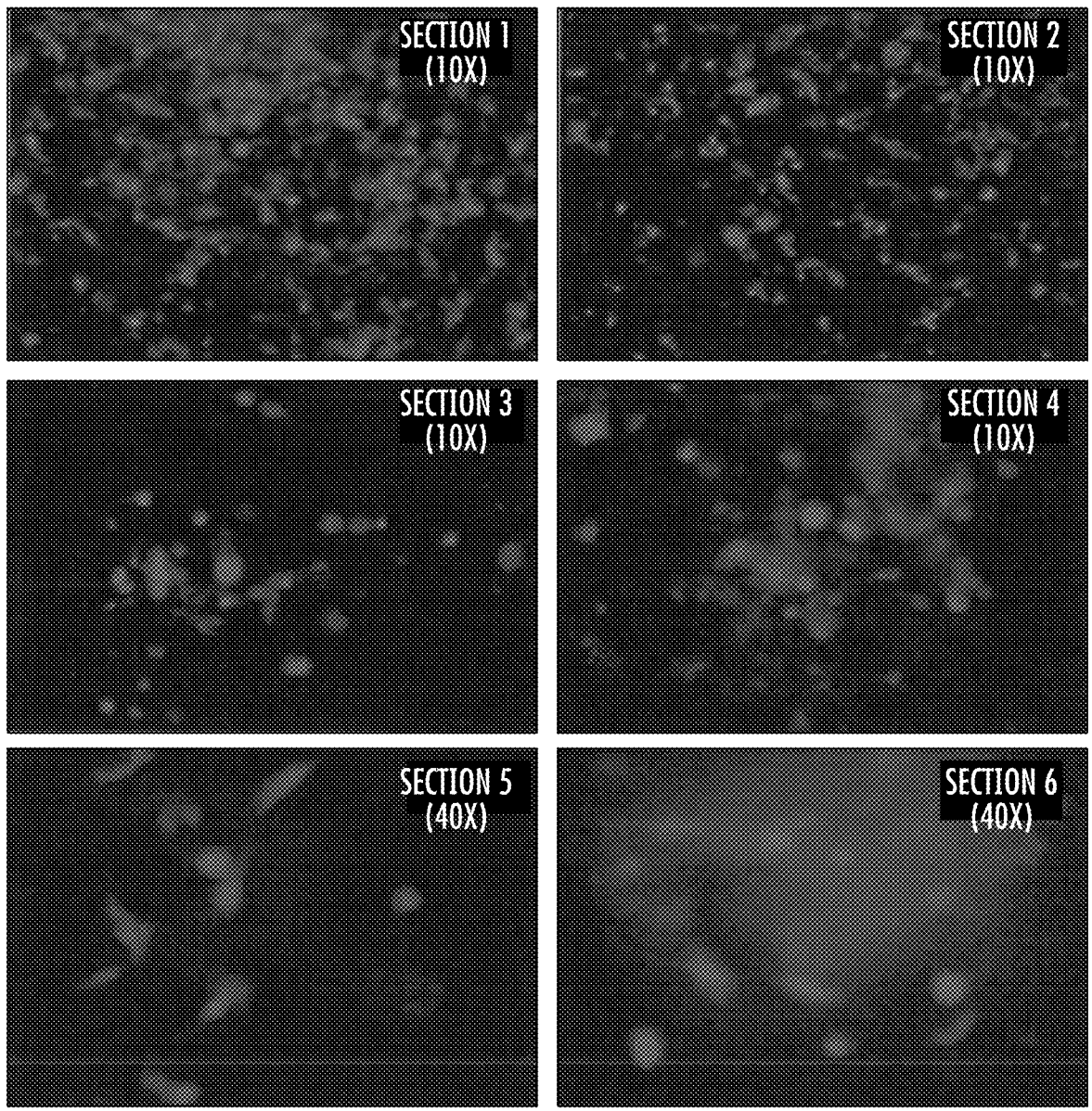
FIG. 10 shows Fluorescence images showing Calcein-AM staining on different cross-sectional sections of Nerve conduit/Matrix.

Example 10: Sectioning of Nerve Conduit/Matrix Scaffold to Check MSCs Proliferation and Migration In an embodiment, Nerve conduit/matrix were into different sections to check MSCs cells adherence and viability on the lumen and outside surface of conduit wall using Calcein-AM stain. Conduit images were captured (FIG. 10) in both vertical and horizontal sections in order to ensure the cells migration.

Figure 11:
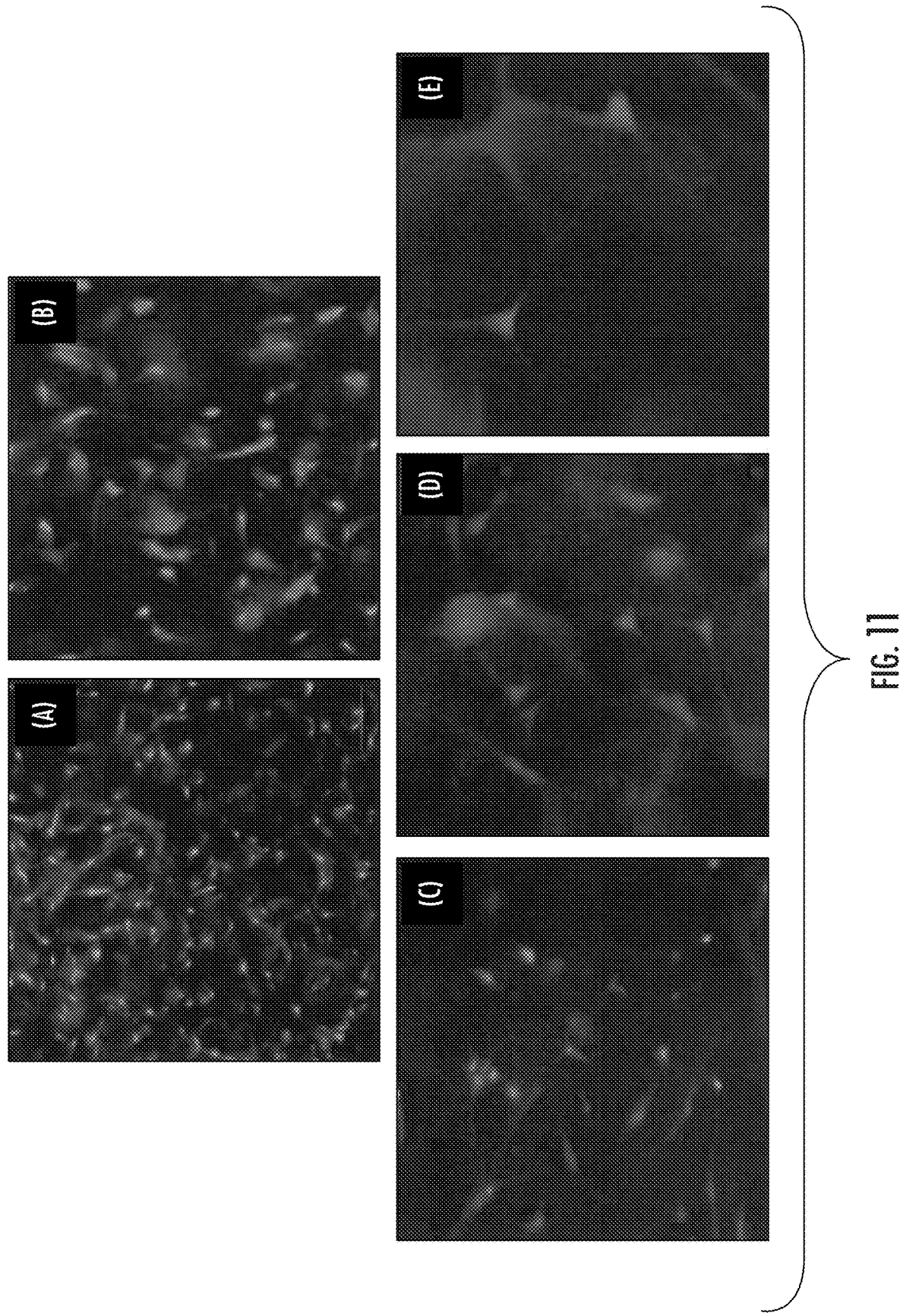
FIG. 11 shows Calcein-AM staining on revived Nerve conduit/Matrix (stored at −80° C. after lyophilization) cryopreserved in cryomedia A, cryomedia B, cryomedia C and cryomedia D on day 4.

Example 11: Cryopreservation and Freeze-Drying of Cell Seeded Nerve Conduit/Matrix In an embodiment, to check cell survival efficiency after freeze-drying (FIG. 11), trehalose was used at a single concentration of 0.5 M in combination with three different concentration of Bovine Serum Albumin (BSA) i.e. 12.5%, 10%, 9.5%. MSCs seeded scaffolds were cryopreserved using freezing media consisted of alpha MEM with 10% FBS along with A) alpha MEM+20% FBS+0.5 M Trehalose dehydrate+12.5% BSA; B) alpha MEM+20% FBS+0.5 M Trehalose dehydrate+10% BSA; C) alpha MEM+20% FBS+ 0.5 M Trehalose dehydrate+9.5% BSA; D) alpha MEM+ 20% FBS+0.5M Trehalose dehydrate alone. Petri dishes containing scaffolds were placed in a freezing solution containing isopropyl alcohol that provided a 1° C./min cooling rate when stored at −80° C. Freeze-drying was done by transferring frozen samples from −80° C. to the temperature-controlled shelves of a lyophilizer. Lyophilization cycle: Lyophilization cycle: Drying 0°, Vacuum 500 mtorr, 48 hrs. cycle. Cryopreserved scaffolds under lyophilized condition in cryomedia media A, B, C, D were revived successfully as shown by calcein staining performed after $4^{th}$ day post revival.

Example 12: In Vitro Differentiation of MSCs into Schwann-Like Cells

Figure 12:
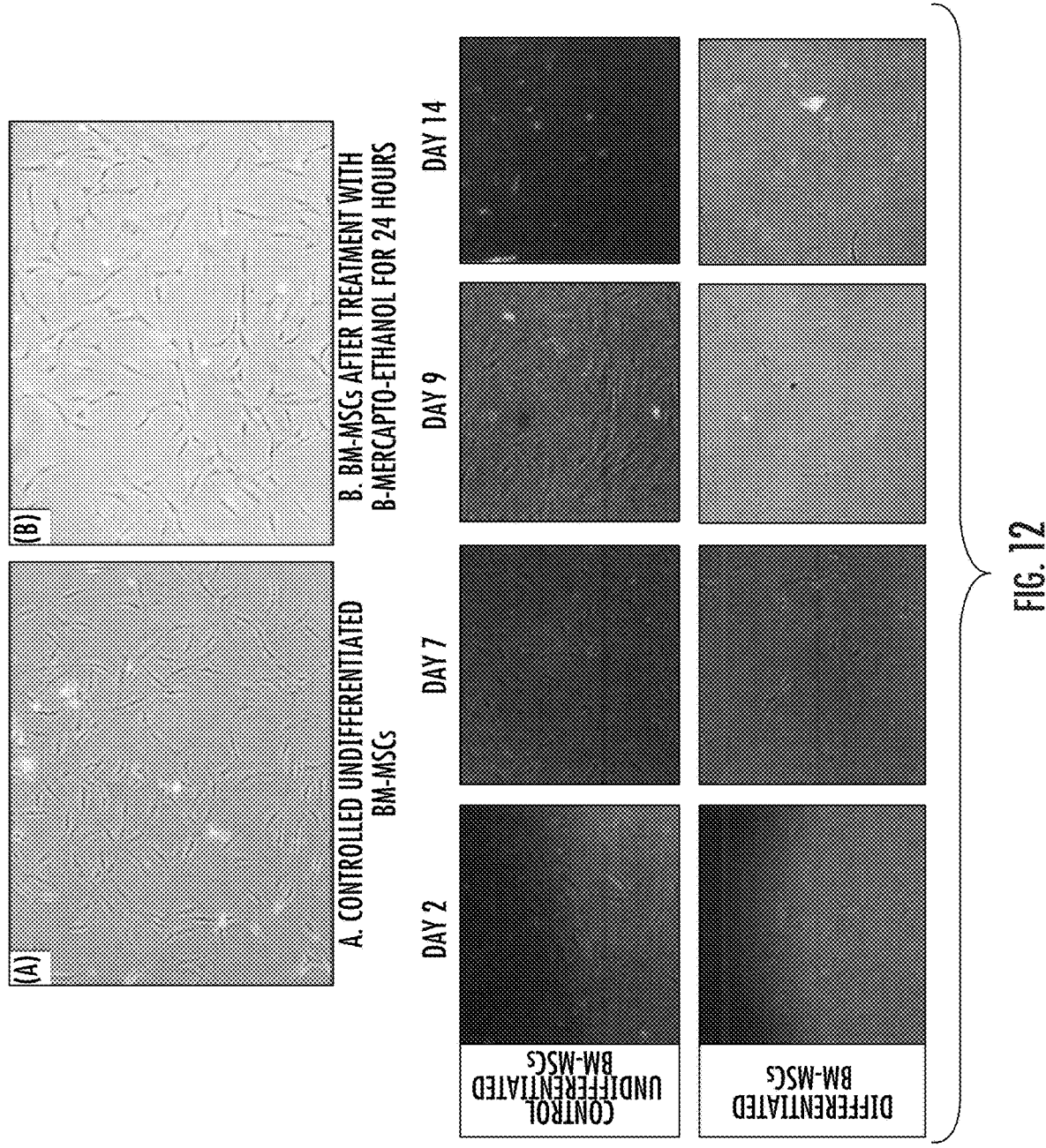
FIG. 12 shows Bright field images showing morphological changes in MSCs during their differentiation into Schwann cells at different time intervals.

In an embodiment, for differentiation, several reagents and trophic factors were applied to induce MSCs into cells with a phenotype similar to that of Schwann cells (FIG. 12) by sequential treatment: first with β-mercaptoethanol (BME), followed by all-trans-retinoic acid (ATRA) treatment, and then culturing the cells in the presence of forskolin (FSK), basic fibroblast growth factor (bFGF), platelet derived growth factor (PDGF), and heregulin growth factor (HRG). Phase-contrast microscopy revealed that the differentiated MSCs were morphologically different from the original undifferentiated MSCs. Cells cultured in the differentiation media changed from a fibroblast-like morphology to an elongated spindle shape (FIG. 12), similar to that of Schwann cells.

Figure 13:
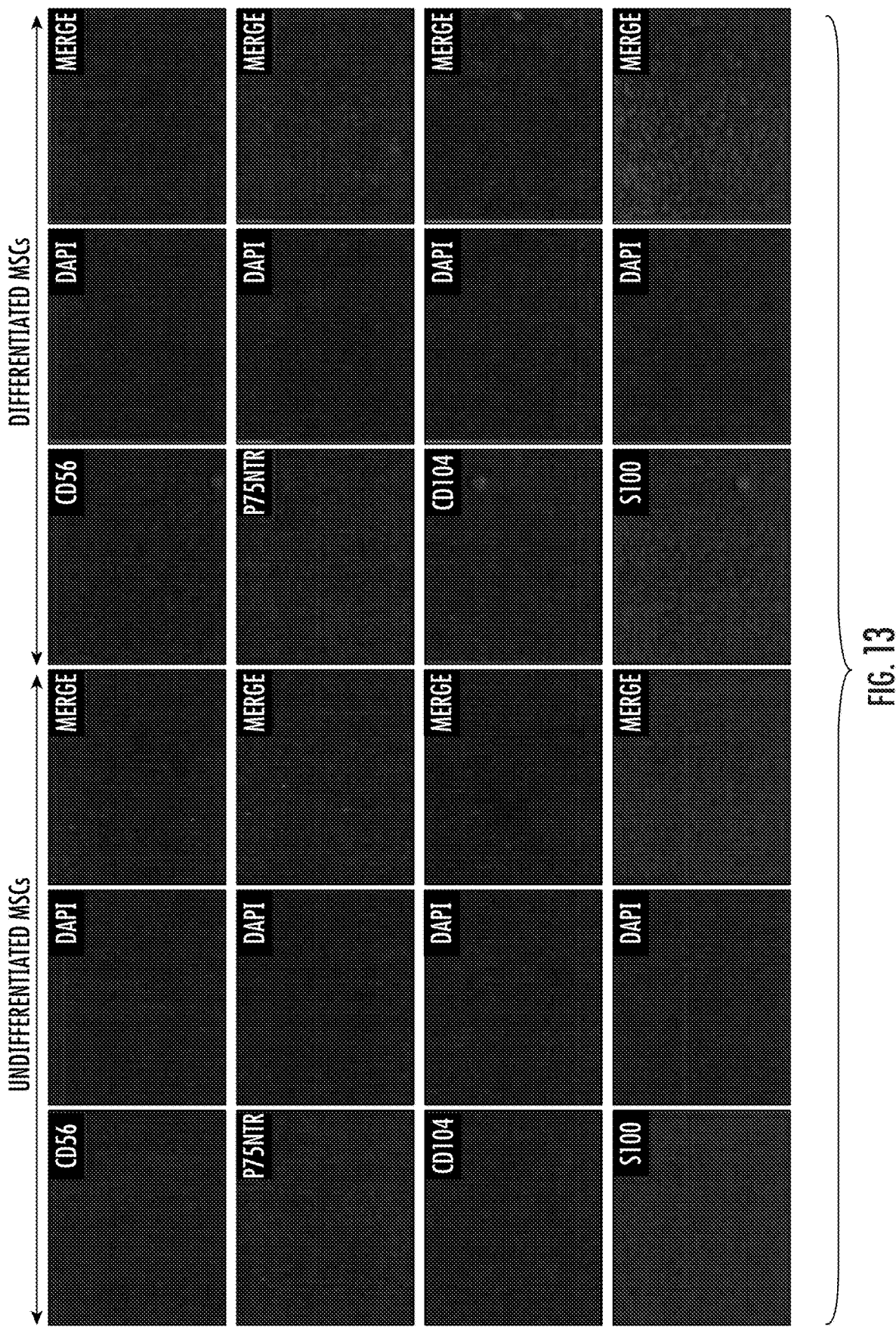
FIG. 13 shows Immunostaining for the Schwann cell markers CD56 (red), p75NGFR (green), CD 104 (red), S100 (green) after 14 days of differentiation. Cell nuclei were stained with DAPI (blue). Scale bars, 100 sm.

In an embodiment, in order to confirm the successful SC differentiation, immunocytochemistry of S-100, p75, CD104 and CD56, all known as markers of Schwann cells was performed. After induction, most of the differentiated SCs were positive for S100, CD56, CD104 and p75 (FIG. 13), in contrast to undifferentiated MSCs.

Example 13: In Vivo Degradation Study of Nerve Conduit/Matrix

Figure 14:
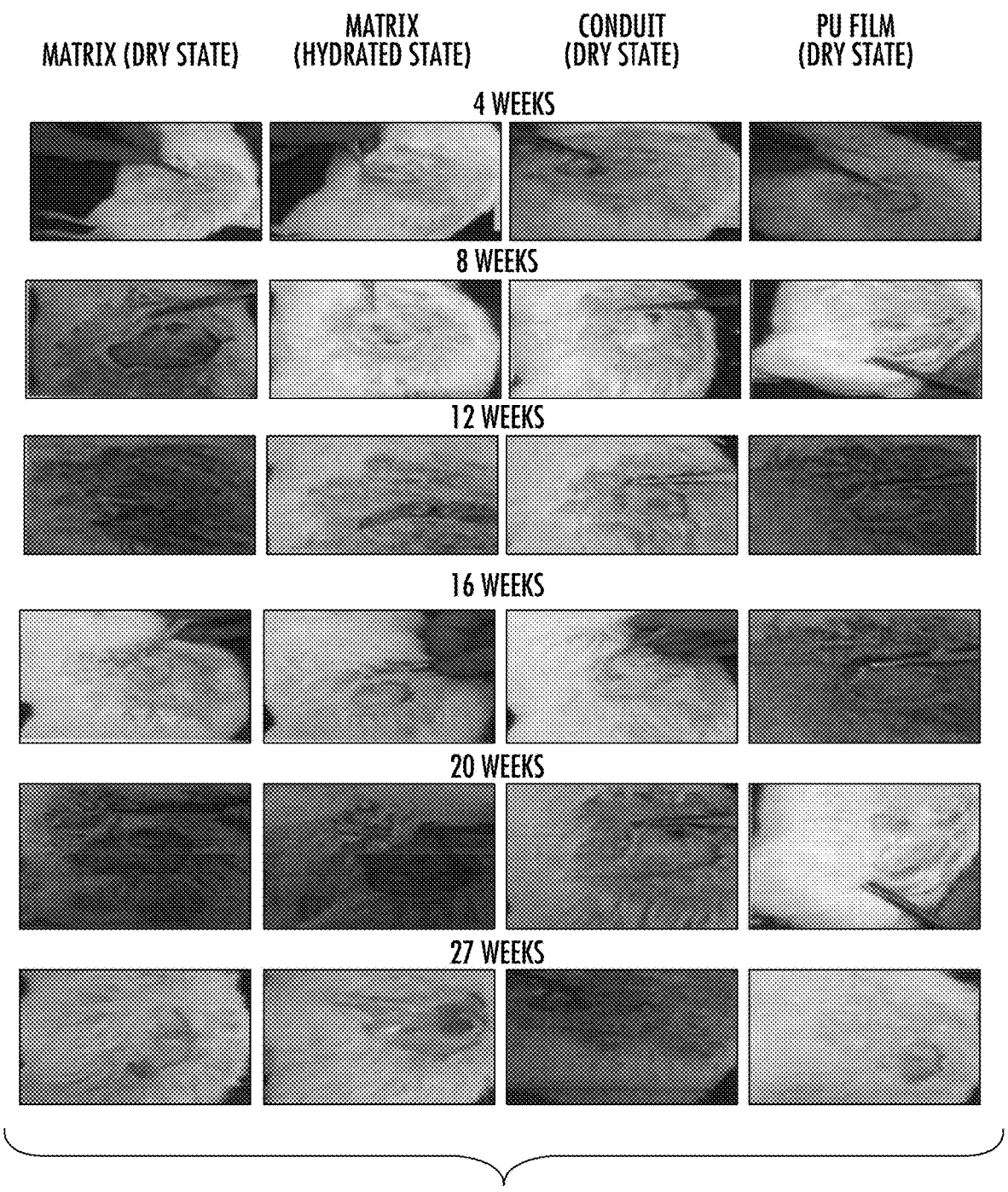
FIG. 14 shows In vivo degradation of nerve conduit and matrix form implanted subcutaneously on the dorsal site of rats at 4, 8, 12, 16, 20 and 27 weeks after implantation.

In an embodiment, for in vivo degradation study, the nerve conduit/matrix in both conduit and sheet form were implanted subcutaneously on the back of SD rats (FIG. 14). At predefined time points (4, 8, 12, 16, 20 and 27 weeks)

after implantation, the test scaffolds were photographed and harvested together with surrounding tissue for histological evaluation. The nerve conduit/matrix was not degraded throughout the implantation period, and remained stable upto 27 weeks post-implantation.

Figure 15:
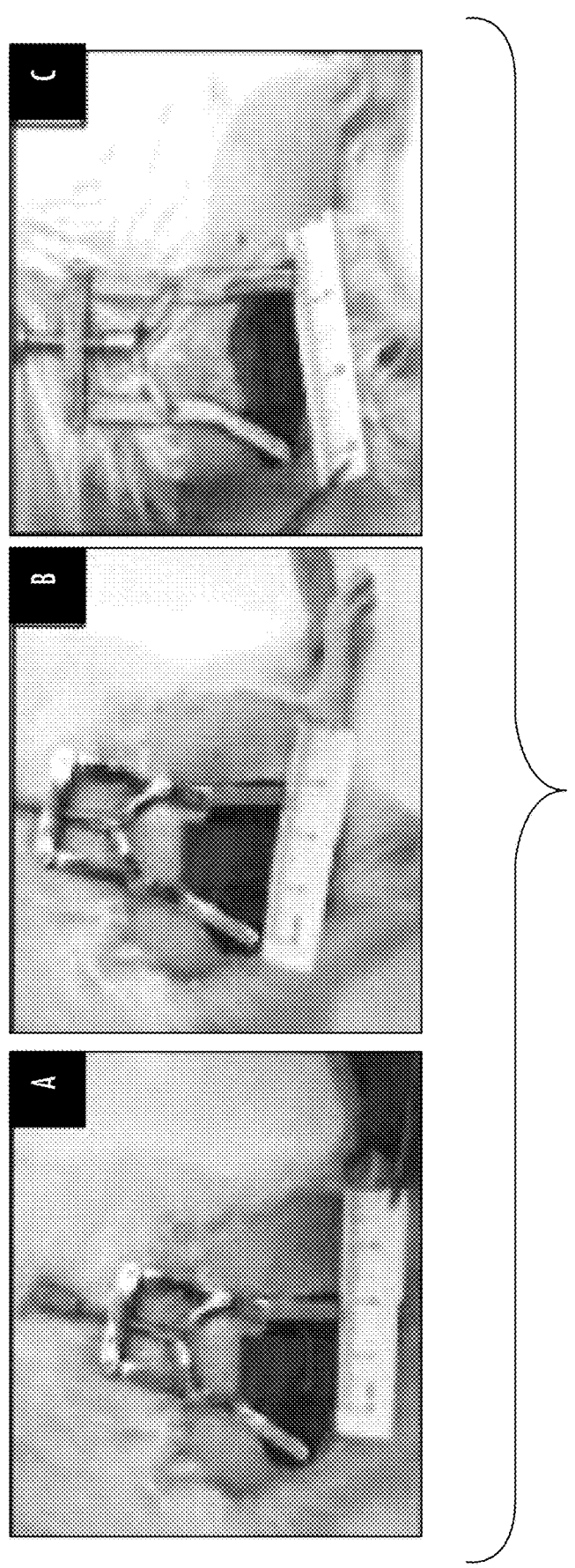
FIG. 15 shows Dissection (A, B) and surgical reconstruction (C) of experimental sciatic nerve injury.

Example 14: In Vivo Implantation to Check the Efficacy of Nerve Conduit/Matrix Pre-Seeded with Differentiated Schwann Cells In an embodiment, the in vivo study was conducted to assess the efficacy of nerve conduit/matrix pre-seeded with mesenchymal stem cells (MSCs) and MSCs differentiated Schwann cells to repair peripheral nerve defect in rat sciatic nerve transection model. The rat sciatic nerve transection model has been commonly used for the evaluation of tissue engineered NGCs in promoting peripheral nerve regeneration in vivo. Before in vivo implantation, in vitro biocompatibility of nerve conduit/matrix with MSCs was investigated. Our initial pilot study to optimize the in vivo experiments was conducted on 15 Sprague Dawley rats. The right sciatic nerve of each animal was transected and a 10 mm segment of the nerve removed thus creating a gap that was bridged with (1) nerve conduit/matrix seeded with either differentiated SCs (nerve conduit/matrix+DSC) or (2) both MSCs and differentiated SCs (nerve conduit/matrix+B2+DSC). The left sciatic nerve remained intact and used later as a control. The efficacy of nerve conduit/matrix was investigated based on the results of walking track analysis, electrophysiology, and histological assessment (FIG. 15).

Example 15: Histological Analysis of Implanted Nerve Conduit/Matrix

Figure 16:
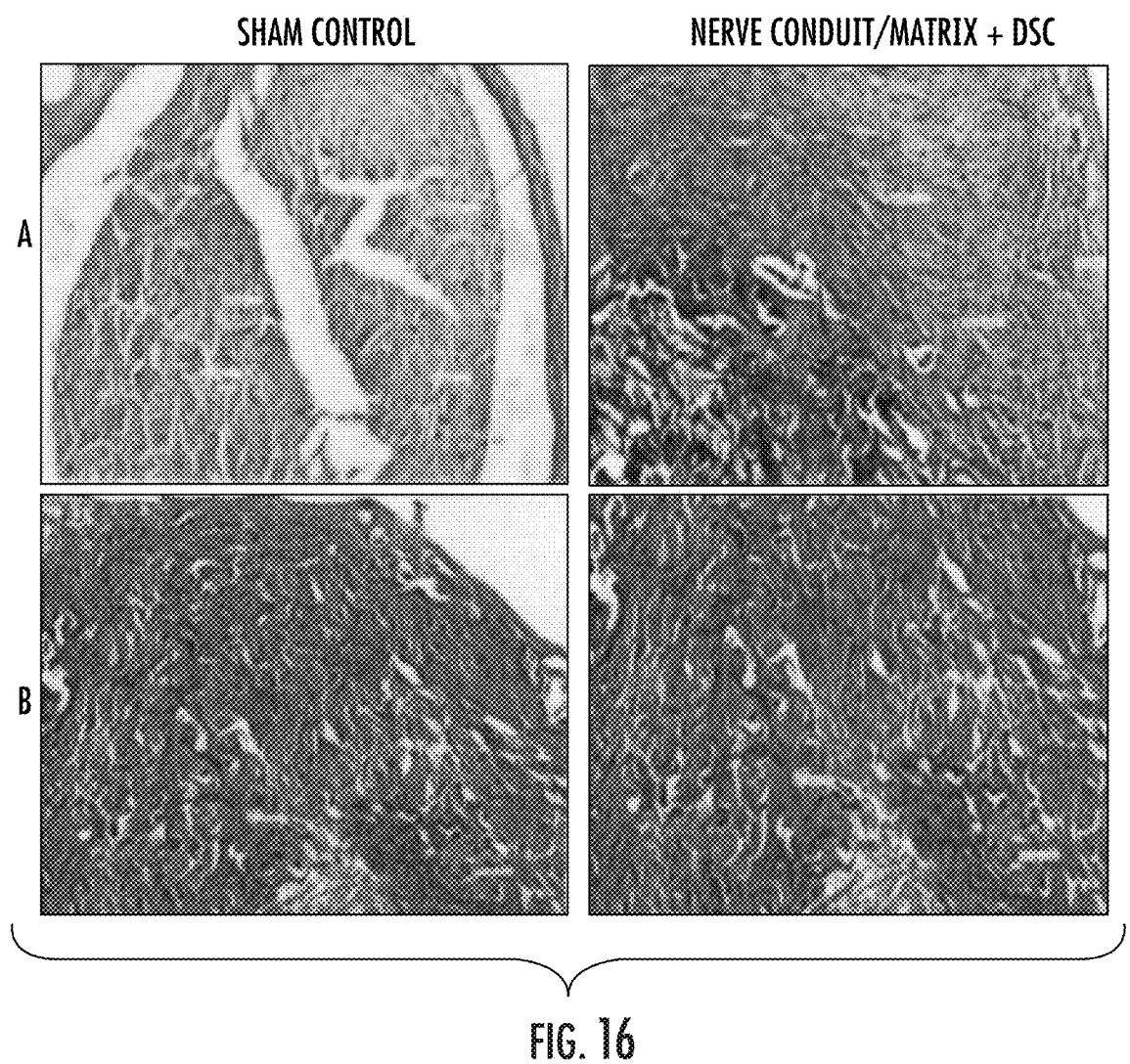
FIG. 16 shows Histological examination of regenerated sciatic nerves after 8 weeks of implantation. (A) H&E staining shown the overview of nerve morphology in each group; (B) Myelination of regenerated nerves revealed by toluidine blue staining (10× magnification).

In an embodiment, for the histological evaluation of nerve regeneration, harvested nerve tissue was sectioned and stained with hematoxylin-eosin and toluidine blue. Morphological observations were carried out at $8^{th}$ weeks post-operatively, detected that regenerated myelinated fibers were smaller and showed a thinner myelin sheath in comparison to normal nerves. The nerve conduit/matrix+DSC group showed distribution of nerve fibers with myelin and fibrous connective tissue (FIG. 16). This group showed irregular shaped perineurium and epineurium, which was largely occupied by fibrous connective tissue with center showing distorted axons with wavy plasma and myelin sheath. In addition, numerous blood vessels were observed around the regenerated nerves. Regeneration of fibrous myelinated nerve is considered important factor in terms of nerve regeneration of damaged nerve. The number of regenerated nerve fibers distal to the NGCs seeded with differentiated SC was fewer in comparison to midpoint of conduit. The nerve conduit/matrix+B2+DSC group displayed growing nerves with less myelinated fibers and thinner myelin sheaths in comparison to nerve conduit/matrix+DSC group. In this group, however, far fewer nerve fibres but a large quantity of connective tissues were visible between the nerve stumps. Besides, infiltration of inflammatory cells was found in the proximal and middle portions of the graft, surrounded by fibrous connective tissue fibers and nerve cell bodies.

In an embodiment, the prepared nerve conduit/matrix is potential substitute in nerve regeneration and repair and it helps in faster restoration of motor and sensory function in nerve injury (peripheral nerve injury, spinal cord injury and any other type of nerve injury). Various experiments were conducted to check the said efficacy of bioengineered nerve conduit/matrix. Cell viability, fluorescence microscopy and scanning electron microscopy results confirm the cell growth and distribution of the cells uniformly in matrix. In vivo studies confirmed the potential nerve regeneration and repair property of conduit.

In an embodiment, the obtained results of the potential and properties of the product of this invention were found considerably efficacious. It clearly indicates the technical advancement as compared to prior art.

Thus, the present invention provides novel and unique technique of culturing human mesenchymal stem cells, mesenchymal stem cells differentiated schwann cells and nerve cells into a proliferating, sub-confluent layer on a lyophilized biocompatible conduit/matrix prepared from plurality of composite polymers by using glutaraldehyde as a cross-linker without any integrated harmful chemicals for direct implantation or delivery of the said human mesenchymal stem cells, wherein in the said invention, the said cells are transferred while in a proliferative state and the final product obtained is transported in semi-solid medium. The said semi-solid medium is agar medium 1% to 3% and cell culture medium with essential growth factors including HEPES 2-3 gm/l and sodium bicarbonate 2-3.5 gm/l. suitable for grafting and provides a better, efficient, easy to use, cost effective ready to use biodegradable and biocompatible artificial nerve conduit/matrix for nerve repair and regeneration with sensory and motor function in a synergistic manner wherein the grafts can be prepared within 12 days.

So accordingly, the present invention provides an improved biodegradable, biocompatible, high porosity three-dimensional artificial nerve conduit/matrix based scaffold polyelectrolyte complex (PEC) with autologous/allogeneic human stem cells for nerve repair and regeneration, and a method of preparing thereof, said scaffold comprising of plurality of composite polymers and using glutaraldehyde as cross-linker, wherein said scaffold is non-adherent, has differential porosity, is able to grow cells directly on the polymeric conduit/matrix (scaffold) for direct implantation or delivery.

In an embodiment, said grafts are prepared within 12 days.

In another embodiment, said scaffolds take forms ranging from sponge like sheets to gels to highly complex structures with intricate pores and channels made with new materials processing technologies such that the spatial and compositional properties of the scaffold, the porosity of the scaffold and interconnectivity of the pores enables cell penetration into the structure as well as the transport of nutrients and waste products with differential porosity helping in the cells attachment and signal transduction.

In another embodiment, said method is comprising a unique technique of culturing human mesenchymal stem cells, mesenchymal stem cells, differentiated schwann cells and nerve cells into a proliferating, sub-confluent layer on a lyophilized biocompatible conduit/matrix, without any integrated harmful chemicals for direct implantation or delivery of the said human mesenchymal stem cells, wherein the cells are transferred while in a proliferative state and the final product obtained is transported in semi-solid medium.

In another embodiment, said nerve conduit/matrix provides repair and regeneration in a synergistic manner.

In another embodiment, said plurality of polymers are preferably selected from but not limited to gelatin, chitosan, collagen, hyaluronic acid, polyvinyl alcohol (PVA), poly caprolactone (PCL), poly pyrrole, poly urethane (PU), poly allyl amine, poly ethylene glycol 200 (PEG 200), gum acacia, guar gum and partially denatured collagen.

In another embodiment, said polymers are in the range of gelatin 1%-10% w/v, chitosan 0.5%-2.5% w/v, hyaluronic acid 0.1%-2% w/v, collagen 0.1/-10% w/v and glutaraldehyde solution 5%-50% v/v with gelatin of 50-300 bloom strength, DAC (dialdehyde cellulose) chitosan ranging from 75%-95%.

In another embodiment, said semi-solid medium is agar medium in the range of 1% to 3% and cell culture medium with essential growth factors including HEPES 2-3 gm/l and sodium bicarbonate 2-3.5 gm/l suitable for grafting which results in a better, efficient, easy to use, cost effective, ready to use biodegradable and biocompatible artificial nerve conduit/matrix for nerve repair and regeneration with sensory and motor function, in a synergistic manner.

In another embodiment, said method of preparing the scaffold comprises physico-chemical treatment; and lyophilization of freeze-dried scaffold.

In another embodiment, said method comprises sequential timed patterned physico-chemical treatment of the four or more polymers to get 3D scaffold of polyelectrolyte complex (PEC) and also at the same time using a specifically designed aspect ratio of a system for agitation/homogenization.

In another embodiment, said method comprises stabilizing the scaffold by cross linking with glutaraldehyde solution and freeze drying.

In another embodiment, said obtained freeze-dried 3D scaffold is stabilized and neutralized by ammonia fumes (5%-25%) for 12-24 hrs in closed chamber to make the stable and functional scaffold for cell seeding.

In another embodiment, said obtained scaffold is freeze-dried to make the stable scaffold for seeding of autologous or allogeneic mesenchymal stem cells (MSCs derived from bone marrow or umbilical cord) Schwann cells and neuronal cells (differentiated form mesenchymal stem cells).

In another embodiment, said mesenchymal stem cell, Schwann cells and neuronal cells are seeded onto biocompatible scaffold at cell density of $0.5 \times 10^5$ to $0.8 \times 10^5$ cell/cm$^2$.

In another embodiment, said cells are monolayer and 80% to 100% confluent at the final stage of product formulation.

In another embodiment, said cells seeded on scaffold are cultured-in with serum and without serum medium.

In another embodiment, said mesenchymal stem cells are autologous or allogeneic or both.

In another embodiment, said mesenchymal stem cells, schwann cells and neuronal cells secrete several growth factors and cytokines (extracellular matrix) helpful in nerve regeneration and repair.

In another embodiment, the final product is transported in semi-solid medium and/or liquid medium or in frozen condition, such that the semi-solid medium/liquid medium provides nutrients and support to matrix and maintains the cell viability of matrix between 70% to 95% at the temperature 4° C. to 37° C. for 15 days.

In another embodiment, said conduit/scaffold is in sheet form and/or hollow cylindrical conduit form.

Advantages of the Invention

The scaffold of the present invention helps in the nerve regeneration and repair.
The present invention comprises of improved healing.
Can be manufactured in any size and shape as per the requirement.
Easy to handle.
Environment friendly as it is degradable easily.
It ensures rapid healing in peripheral nerve injury.
It ensures faster recovery and repair of motor and sensory function.
The grafts can be made within 12 days.
It is economical and offers an alternative treatment to the standard nerve injury treatment methods.
There is a dramatically reduced risk of transmission of infectious disease due to rigorous process controls.
It helps in restoration of motor and sensory function of damaged tissue.

We claim:

1. An artificial tissue construct for nerve repair and regeneration, comprising:
   a lyophilized, physico-chemical treated, biocompatible and biodegradable nerve conduit matrix comprising cross-linked composite polymers comprising 1%-10% w/v of gelatin having 50-300 bloom strength, 0.5%-2.5% w/v of chitosan, 0.1%-2% w/v of hyaluronic acid, 0.1%-10% w/v of collagen based on the total weight of the nerve conduit matrix, wherein a cross-linker comprising 5%-50% w/v of glutaraldehyde solution based on the total weight of the nerve conduit matrix forms the cross-linked composite polymers, wherein said nerve conduit matrix is formed as a three-dimensional scaffold polyelectrolyte complex (PEC) and configured into a hollow cylindrical conduit form having open and interconnected pores of different sizes to facilitate vascularization and nutrient exchange for nerve regrowth; and
   human mesenchymal stem cells at passage 2 to passage 5, differentiated by sequential treatment with B-mercaptoethanol (BME), followed by all-trans-retonoic acid (ATRA) and then platelet derived growth factor (PDGF), basic fibroblast growth factor (bFGF), and heregulin growth factor (HRG) into elongated, spindle shaped Schwann cell phenotypes seeded and grown onto the hollow cylindrical conduit at a cell density of $0.5 \times 10^5$ to $0.8 \times 10^5$ cell/cm$^2$ to form a subconfluent, monolayer that is 80% to 100% confluent for direct implantation or delivery.

2. The artificial tissue construct according to claim 1, wherein said biocompatible and biodegradable nerve guidance matrix further comprises at least one of polycaprolactone (PCL), polypyrrole, polyurethane (PU), polyallylamine, polyethyleneglycol 200 (PEG 200), gum acacia, guar gum and partially denatured collagen.

3. The artificial tissue construct according to claim 1, wherein said three-dimensional scaffold PEC is freeze-dried.

4. The artificial tissue construct according to claim 1, comprising a semi-solid transport medium on which the biocompatible and biodegradable nerve guidance matrix is supported, wherein the semi-solid transport medium comprises an agar medium comprising HEPES at a concentration of 2-3 g/L and sodium bicarbonate at a concentration of 2-3.5 g/L.

5. An artificial tissue construct for nerve repair and regeneration, comprising:
   a lyophilized, physico-chemical treated, biocompatible and biodegradable nerve guidance matrix comprising cross-linked composite polymers comprising 1%-10% w/v of gelatin having 50-300 bloom strength, 0.5%-2.5% w/v of chitosan, 0.1%-2% w/v of hyaluronic acid, 0.1%-10% w/v of collagen based on the total weight of the nerve conduit matrix, wherein a cross-linker comprising 5%-50% w/v of glutaraldehyde solution based on the total weight of the nerve conduit matrix forms the cross-linked composite polymers, wherein said nerve conduit matrix is formed as a three-dimensional scaffold polyelectrolyte complex (PEC) and configured into a hollow cylindrical conduit form having open and interconnected pores of different sizes to facilitate vascularization and nutrient exchange for nerve regrowth; and human mesenchymal stem cells differentiated by sequential treatment with B-mercaptoethanol (BME), followed by all-trans-retonoic acid (ATRA) and then platelet derived growth factor (PDGF), basic fibroblast growth factor (bFGF), and heregulin growth factor (HRG) into elongated, spindle shaped Schwann cell phenotypes seeded and grown onto the hollow cylindrical conduit at a cell density of $0.5 \times 10^5$ to $0.8 \times 10^5$ cell/cm$^2$ to form a subconfluent, monolayer for direct implantation or delivery.

6. The artificial tissue construct according to claim 5, wherein said biocompatible and biodegradable nerve guidance matrix further comprises at least one of polycaprolactone (PCL), polypyrrole, polyurethane (PU), polyallylamine, polyethyleneglycol 200 (PEG 200), gum acacia, guar gum and partially denatured collagen.

7. The artificial tissue construct according to claim 5, wherein said three-dimensional scaffold PEC is freeze-dried and said subconfluent and grown monolayer of human mesenchymal stem cells differentiated into elongated, spindle shaped Schwann cell phenotypes on the biocompatible and biodegradable nerve guidance matrix are 80% to 100% confluent.

8. The artificial tissue construct according to claim 5, comprising a semi-solid transport medium on which the biocompatible and biodegradable nerve guidance matrix is supported, wherein the semi-solid transport medium comprises an agar medium comprising HEPES at a concentration of 2-3 g/L and sodium bicarbonate at a concentration of 2-3.5 g/L.

* * * * *